US010435667B2

(12) United States Patent
Canto-Soler et al.

(10) Patent No.: US 10,435,667 B2
(45) Date of Patent: Oct. 8, 2019

(54) METHODS FOR FORMING THREE-DIMENSIONAL HUMAN RETINAL TISSUE IN VITRO

(71) Applicant: THE JOHNS HOPKINS UNIVERSITY, Baltimore, MD (US)

(72) Inventors: Maria Valeria Canto-Soler, Washington, DC (US); Xiufeng Zhong, Timonium, MD (US)

(73) Assignee: The Johns Hopkins University, Baltimore, MD (US)

( * ) Notice: Subject to any disclaimer, the term of this patent is extended or adjusted under 35 U.S.C. 154(b) by 175 days.

(21) Appl. No.: 15/111,883

(22) PCT Filed: Jan. 16, 2015

(86) PCT No.: PCT/US2015/011701
§ 371 (c)(1),
(2) Date: Jul. 15, 2016

(87) PCT Pub. No.: WO2015/109148
PCT Pub. Date: Jul. 23, 2015

(65) Prior Publication Data
US 2016/0333312 A1    Nov. 17, 2016

Related U.S. Application Data

(60) Provisional application No. 61/928,116, filed on Jan. 16, 2014.

(51) Int. Cl.
C12N 5/0793    (2010.01)

(52) U.S. Cl.
CPC ........ *C12N 5/062* (2013.01); *C12N 2501/385* (2013.01); *C12N 2506/45* (2013.01); *C12N 2509/00* (2013.01); *C12N 2533/90* (2013.01)

(58) Field of Classification Search
CPC .......... C12N 2501/385; C12N 2506/45; C12N 2509/00; C12N 2533/90; C12N 5/062
See application file for complete search history.

(56) References Cited

U.S. PATENT DOCUMENTS

2010/0105137 A1    4/2010    Takahashi et al.

FOREIGN PATENT DOCUMENTS

WO    2008045952 A2    4/2008
WO    2011055855 A1    5/2011

OTHER PUBLICATIONS

Pankratz et al. (2007) Stem Cells 25: 1511-1520 (Year: 2007).*
Gamm (2008) Invest OphthalmolVisSci 49(2): 788-799 (Year: 2008).*
Borooah, S., et al. (2013) "Using human induced pluripotent stem cells to treat retinal disease", Progress in Retinal and Eye Research, vol. 37, pp. 163-181.
Eiraku, M., et al. (2011) "Self-organizing optic-cupmorphogenesis in three-dimensional culture", Nature, vol. 472, pp. 51-58.
Gamm, D., et al. (2013) "Modeling retinal degenerative diseases with human iPS-derived cells: current status and future implications", Expert Rev. Ophthalmol., vol. 8, No. 3, pp. 213-216.
Nakano, T., et al. (2012) "Self-Formation of Optic Cups and Storable Stratified Neural Retina from Human ESCs", Cell Stem Cell, vol. 10, pp. 771-785.
Zhong, X., et al. (2013) "Generation of three-dimensional retinal tissue with functional photoreceptors from human PSCs", Nature Communications, vol. 5, Article No. 4047.
Hartong et al., Retinitis pigmentosa. Lancet 368, 1795-1809 (2006).
Ramsden et al., Stem cells in retinal regeneration: past, present and future. Development 140, 2576-2585 (2013).
Stern et al., Stem cells for retinal replacement therapy. Neurotherapeutics : the journal of the American Society for Experimental NeuroTherapeutics 8, 736-743 (2011).
Cramer et al., Translating induced pluripotent stem cells from bench to bedside: application to retinal diseases. Current gene therapy 13, 139-151 (2013).
Eiraku et al., Self-organizing optic-cup morphogenesis in three-dimensional culture. Nature 472, 51-56 (2011).
Nakano et al., Self-formation of optic cups and storable stratified neural retina from human ESCs. Cell Stem Cell 10, 771-785 (2012).
Adler et al., Molecular mechanisms of optic vesicle development: complexities, ambiguities and controversies. Dev Biol 305, 1-13 (2007).
Bassett et al., Cell fate determination in the vertebrate retina. Trends in neurosciences 35, 565-573 (2012).
Lamba et al., Efficient generation of retinal progenitor cells from human embryonic stem cells. Proc Natl Acad Sci USA 103, 12769-12774 (2006).
Osakada et al., Toward the generation of rod and cone photoreceptors from mouse, monkey and human embryonic stem cells. Nat Biotechnol 26, 215-224 (2008).
Osakada et al., in vitro differentiation of retinal cells from human pluripotent stem cells by small-molecule induction. J Cell Sci 122, 3169-3179 (2009).
Tucker et al., Patient-specific iPSC-derived photoreceptor precursor cells as a means to investigate retinitis pigmentosa. eLife 2, e00824 (2013).

(Continued)

*Primary Examiner* — Lisa J Hobbs
(74) *Attorney, Agent, or Firm* — Johns Hopkins Technology Ventures

(57) ABSTRACT

The present invention relates to the field of stem cells. More specifically, the invention provides methods and compositions useful for forming three-dimensional human retinal tissue in vitro. In a specific embodiment, an in vitro method for differentiating hiPSCs into three-dimensional retinal tissue comprising functional photoreceptors comprises the steps of (a) culturing the hiPSCs to form aggregates; (b) transitioning the aggregates into a neural induction medium; (c) seeding the aggregates on to extracellular matrix coated cell culture substrates; (d) replacing NIM with a chemically-defined differentiation medium; (e) detaching NR domains; (f) culturing in suspension; and (g) adding animal serum or plasma component and retinoic acid.

42 Claims, 11 Drawing Sheets
Specification includes a Sequence Listing.

(56) References Cited

OTHER PUBLICATIONS

Tucker et al., Use of a synthetic xeno-free culture substrate for induced pluripotent stem cell induction and retinal differentiation. Stem cells translational medicine 2, 16-24 (2013).
Boucherie et al., Brief report: self-organizing neuroepithelium from human pluripotent stem cells facilitates derivation of photoreceptors. Stem Cells 31, 408-414 (2013).
Zuber., Eye field specification in Xenopus laevis. Curr Top Dev Biol 93, 29-60 (2010).
Zhang et al., Pax6 is a human neuroectoderm cell fate determinant. Cell Stem Cell 7, 90-100 (2010).
Pevny et al., A role for SOX1 in neural determination. Development 125, 1967-1978 (1998).
Xia et al., Differentiation of neuroepithelia from human embryonic stem cells. Methods Mol Biol 549, 51-58 (2009).
Nguyen et al., Signaling and transcriptional regulation in early mammalian eye development: a link between FGF and MITF. Development 127, 3581-3591 (2000).
Horsford et al., Chx10 repression of Mitf is required for the maintenance of mammalian neuroretinal identity. Development 132, 177-187 (2005).
Meyer et al., Modeling early retinal development with human embryonic and induced pluripotent stem cells. PNAS 2009.
Prada et al., Spatial and Temporal Patterns of Neurogenesis in the Chick Retina. Eur J Neurosci 3, 559-569 (1991).
Cepko et al., Cell fate determination in the vertebrate retina. Proc Natl Acad Sci U S A 93, 589-595 (1996).
Stenkamp et al., Retinoid effects in purified cultures of chick embryo retina neurons and photoreceptors. Invest Ophthalmol Vis Sci 34, 2425-2436 (1993).
Stevens et al., Plasticity of photoreceptor-generating retinal progenitors revealed by prolonged retinoic acid exposure. BMC Dev Biol 11, 51 (2011).
Hendrickson et al. Rod photoreceptor differentiation in fetal and infant human retina. Exp Eye Res 87, 415-426 (2008).
Hollenberg et al., Human retinal development: ultrastructure of the outer retina. The American journal of anatomy 137, 357-385 (1973).
Sasai et al., in vitro organogenesis in three dimensions: self-organising stem cells. Development. Nov. 2012;139(22):4111-21.
Meyer et al., Optic Vesicle-like Structures Derived from Human Pluripotent Stem Cells Facilitate a Customized Approach to Retinal Disease Treatment. Stem Cells 29, 1206-18 (2011).
Phillips et al., Blood-derived human iPS cells generate optic vesicle-like structures with the capacity to form retinal laminae and develop synapses. Invest Ophthalmol Vis Sci 53, 2007-2019 (2012).
Gutierrez et al., Cytoskeleton proteins previously considered exclusive to Ganglion Cells are transiently expressed by all retinal neuronal precursors. BMC Dev Biol 11, 46 (2011).
Megason et al., A mitogen gradient of dorsal midline Wnts organizes growth in the CNS. Development 129, 2087-2098 (2002).
Burridge et al., A universal system for highly efficient cardiac differentiation of human induced pluripotent stem cells that eliminates interline variability. PLoS ONE 6, e18293 (2011).
Park et al., Growth factor-activated stem cell circuits and stromal signals cooperatively accelerate non-integrated PSC reprogramming of human myeloid progenitors. PLoS One 7, e42838 (2012).
Yan et al., Early expression of recoverin in a unique population of neurons in the human retina. Anatomy and embryology 195, 51-63 (1997).
Glubrecht et al., Differential CRX and OTX2 expression in human retina and retinoblastoma. J Neurochem 111, 250-263 (2009).
Lagar'Kova et al., In vitro histogenesis of human embryonic stem cells into retina components. Bull Exp Biol Med. Feb. 2012;152(4):516-8.
Santo-Soler, V., et al., "Development of 3D-retinal cups from human iPS cells", MSCRS Presentation (2012).
Canto-Soler, V., et al., "Development of 3D-retinal cups from human iPS cells" Manuscript, MSCRS Presentation (2012).
Canto-Soler, V., et al.,"Differentiation of hiPSC into 3D-stratified retinal cups" Gordon Conference Poster (2012).

* cited by examiner

METHODS FOR FORMING THREE-DIMENSIONAL HUMAN RETINAL TISSUE IN VITRO

CROSS-REFERENCE TO RELATED APPLICATIONS

This application is a 35 U.S.C. § 371 U.S. national entry of International Application PCT/US2015/011701, having an international filing date of Jan. 16, 2015, which claims the benefit of U.S. Provisional Application No. 61/928,116, filed Jan. 16, 2014, the content of each of the aforementioned applications is herein incorporated by reference in their entirety.

FIELD OF THE INVENTION

The present invention relates to the field of stem cells. More specifically, the invention provides methods and compositions useful for forming three-dimensional human retinal tissue in vitro.

INCORPORATION-BY-REFERENCE OF MATERIAL SUBMITTED ELECTRONICALLY

This application contains a sequence listing. It has been submitted electronically via EFS-Web as an ASCII text file entitled "P12243-02.txt." The sequence listing is 3,331 bytes in size, and was created on Jan. 16, 2015. It is hereby incorporated by reference in its entirety.

BACKGROUND OF THE INVENTION

Retinal degenerative diseases are a group of clinical conditions in which the dysfunction and death of retinal photoreceptor cells lead to vision loss, and sometimes, total blindness. The development of human induced pluripotent stem cells (hiPSCs) in 2007 roused great hope for their potential use in therapeutic treatments. However, a reliable, efficient method to induce hiPSCs to differentiate into retinal tissue containing functional photoreceptors has not been so far achieved.

SUMMARY OF THE INVENTION

Many forms of blindness result from the dysfunction or loss of retinal photoreceptors[1]. Stem cells, especially induced pluripotent stem cells (iPSCs), may hold great promise for the modeling and/or therapy of diseases[2-4]. Previous work has shown that, when provided with the appropriate cues, mouse and human embryonic stem (ES) cells in culture can develop into a 3-dimensional eyecup that remarkably resembles the vertebrate eye, including differentiation of photoreceptor-like cells[5,6]. Nonetheless, structural and molecular features characteristic of advanced photoreceptor differentiation, such as the formation of outer-segment discs and photosensitivity in these in vitro preparations, have not yet been observed. The present inventors report here that, with a new, highly-simplified procedure, hiPSCs in vitro can recapitulate spatiotemporally each of the main steps of retinal development in vivo and form 3-dimensional retinal cups. Moreover, the photoreceptors in our hiPSC-derived retinal tissue achieve advanced maturation, showing the beginning of outer-segment-disc formation and photosensitivity.

The present invention is based, at least in part, on the development of a protocol to direct hiPSCs to differentiate into retinal cells and form human retinal tissue in vitro. The present inventors hereby present the first methods to obtain 3D-retinal tissue comprising functional photoreceptors in vitro from hiPSCs. More specifically, the retinal tissue contains all major retinal cell types properly laminated including advanced-differentiated photoreceptors. The protocol induces hiPSCs to recapitulate in vitro each of the main steps leading to retinal development in the human embryo in vivo. The system recapitulates retinal development not only at the cellular level, but also at the histoarchitectural level. The system does not use growth factors and/or inhibitors/promoters to induce retinal cell fate specification The protocol does not use MEF as feeder cells to culture hiPSCs, thus providing a system less exposed to potential contamination from animal sources and making it better fitted for future clinical applications. The protocol is the simplest and most cost-effective so far to obtain retinal tissue in vitro.

The methods and compositions of the present invention can be used to study mechanisms regulating human retina development. hiPSCs derived from patients affected by retinal degenerative diseases can be used to study mechanisms underlying these diseases. Moreover, the present invention can be used to screen for molecules with potential therapeutic effects in patients with retinal degenerative diseases. In other embodiments, the present invention can be used to generate human retinal tissue for cell therapy or tissue transplantation to treat patient with retinal diseases.

As described herein, the present invention allows for the production of "human retinas in a dish" derived from hiPSCs. These "human retinas in a dish" can be derived from patient-specific hiPSCs, which could in turn be used for autologous retinal transplantation and/or "custom drug discovery".

Accordingly, in one aspect, the present invention provides in vitro methods for differentiating human induced pluripotent stem cells (hiPSCs) into three-dimensional retinal tissue comprising functional photoreceptors. In one embodiment, the method comprises the steps of (a) on day 0 of differentiation, (i) enzymatically detaching hiPSCs cultured on extracellular matrix-coated cell culture substrates with feeder-free cell culture medium, and (ii) culturing the hiPSCs in suspension to induce formation of aggregates; (b) during days 1-3 of differentiation, transitioning the aggregates into neural induction medium (NIM); (c) during day 6 or 7, seeding the aggregates on to extracellular matrix-coated cell culture substrates; (d) at any time between day 14 and day 17, replacing NIM with a chemically-defined differentiation medium; (e) during the fourth week of differentiation (any of days 22-28), (i) detaching neural retina (NR) domains, and (ii) culturing in suspension; (f) during the fifth or sixth week of differentiation (any of days 29-42), adding animal serum or plasma component to promote cell survival; and (g) at any time between week 5 and week 14 (any of days 29-98), adding all-trans retinoic acid to induce photoreceptor maturation. Step (b) of the method can be performed at any time during day 1, day 2 or day 3. Step (d) can be performed at any time between day 14 and day 17. In particular embodiments, step (d) is performed on day 14, day 15, day 16 or day 17.

In a specific embodiment, the all-trans retinoic acid of step (g) is added at a concentration of about 1 µM. In other embodiments, the all-trans retinoic acid is added at a concentration ranging from about 0.5 µM to about 2.0 µM. In certain embodiments, the all-trans retinoic acid of step (g) is added for a period of about 30 days. In other embodiments, the retinoic acid is added for a period of about 20-40 days, about 25-35 days, and the like including 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, and 40 days or more. In particular embodiments, the method further comprises the step of (h) decreasing the concentration of all-trans retinoic acid to about 0.5 µM. In yet another embodiment, the all-trans retinoic acid is added at any time between week 9 and week 10 (any of days 57-70) at a concentration of about 1 µM and then decreased to about 0.5 µM at any time between week 13 and week 14 (any of days 85-98). In an alternative embodiment, the all-trans retinoic acid is added on day 63 at a concentration of about 1 µM and then decreased to about 0.5 µM at any time between day 90 and day 98. In a further embodiment, the all-trans retinoic acid is added at any time between week 5 and week 6 (any of days 29-42) at a concentration of about 1 µM and then decreased to about 0.5 µM at any time between week 13 and week 14 (any of days 85-98). In another specific embodiment, the all-trans retinoic acid is added on day 42 at a concentration of about 1 µM and then decreased to about 0.5 µM at any time between day 90 and day 98. The concentration of retinoic acid (either or both of the about 1 µM and 0.5 µM concentrations) can be adjusted by one of ordinary skill in the art to achieve the desired effect. For example, the present invention contemplates using an amount of retinoic acid above or below the about 1 µM or 0.5 µM (as the case may be) including 0.5, 0.6, 0.7, 0.8, 0.9, 1.1, 1.2, 1.3, 1.4 or 1.5 µM (or for 0.5 µM, 0.1, 0.2, 0.3, 0.4, 0.6, 0.7, 0.8, 0.9 or 1.0 µM). Further, the amount of retinoic acid can be above or below about 2 µM, including 1.6, 1.7, 1.8, 1.9, 2.0, 2.1, 2.2, 2.3, 2.4, 2.5 and the like.

In one embodiment, the enzymatic detachment of step (a)(i) is accomplished using dispase. In other embodiments, the extracellular matrix is Matrigel™. The cell culture substrate can be a flask, plate or petri dish. In a specific embodiment, the feeder-free cell culture medium is mTeSR™ 1 medium. In another specific embodiment, the NIM of step (b) comprises Dulbecco's modified eagle medium (DMEM)/F12 (1:1), 1% N2 supplement, 1× minimum essential media-non essential amino acids (NEAA), and 2 µg ml$^{-1}$ heparin. The chemically-defined differentiation medium of step (d) can comprise DMEM/F12 (3:1), 2% B27 (without vitamin A), 1× minimum essential media-non essential amino acids (NEAA), and 1% antibiotic-antimycotic.

In another embodiment, the detachment of step (e) comprises manual detachment. In particular embodiments, the animal serum or plasma component is fetal bovine serum. In certain embodiments, the hiPSCs are selected from the group consisting of CB-iPSC6.2, KA.1 and IMR90-4. It is understood that the present invention can be used to differentiate other hiPSCs. The present invention also provides the three-dimensional retinal tissue produced by the methods described herein.

In another specific embodiment, an in vitro method for differentiating hiPSCs into three-dimensional retinal tissue comprising functional photoreceptors comprises the steps of (a) culturing the hiPSCs to form aggregates; (b) transitioning the aggregates into a neural induction medium; (c) seeding the aggregates on to extracellular matrix coated cell culture substrates; (d) replacing NIM with a chemically-defined differentiation medium; (e) detaching NR domains; (f) culturing in suspension; and (g) adding animal serum or plasma component and retinoic acid.

In a specific embodiment, the hiPSCs were cultured on extracellular matrix coated cell culture substrates with feeder-free cell culture medium and enzymatically detached prior to step (a). In particular embodiments, the extracellular matrix is Matrigel™. In another embodiment, the feeder-free cell culture medium is mTeSR™ 1 medium. The cell culture substrate can be a flask, plate or petri dish. In certain embodiments, the enzymatic detachment step is accomplished using dispase. In other embodiments, step (b) is performed during days 1-3 of differentiation.

In a specific embodiment, the NIM of step (b) comprises Dulbecco's modified eagle medium (DMEM)/F12 (1:1), 1% N2 supplement, 1× minimum essential media-non essential amino acids (NEAA), and 2 µg ml$^{-1}$ heparin. Step (c) can be performed during day 6 or 7. Further, step (d) can be performed at any time between day 14 and day 17. In certain embodiments, the chemically-defined differentiation medium of step (d) comprises DMEM/F12 (3:1), 2% B27 (without vitamin A), 1× minimum essential media-non essential amino acids (NEAA), and 1% antibiotic-antimycotic. In other embodiments, the detachment of step (e) comprises manual detachment. The animal serum or plasma component can be any animal serum or plasma component including, but not limited to, fetal bovine serum.

In certain embodiments, the all-trans retinoic acid of step (g) is added at a concentration of about 1 µM. In a specific embodiment, the all-trans retinoic acid of step (g) is added for a period of about 30 days. In other embodiments, the method further comprises the step of (h) decreasing the concentration of all-trans retinoic acid to about 0.5 µM. In a specific embodiment, the all-trans retinoic acid is added at any time between week 9 and week 10 at a concentration of about 1 µM and then decreased to about 0.5 µM at any time between week 13 and week 14. In another embodiment, the all-trans retinoic acid is added on day 63 at a concentration of about 1 µM and then decreased to about 0.5 µM at any time between day 90 and day 98.

In an alternative embodiment, the all-trans retinoic acid is added at any time between week 5 and week 6 at a concentration of about 1 µM and then decreased to about 0.5 µM at any time between week 13 and week 14. In yet another embodiment, the all-trans retinoic acid is added on day 42 at a concentration of about 1 µM and then decreased to about 0.5 µM at any time between day 90 and day 98. In certain embodiments, the hiPSCs are selected from the group consisting of CB-iPSC6.2, KA.1 and IMR90-4. The present invention also provides the three-dimensional retinal tissue produced by the methods described herein.

The present invention also provides an in vitro method for differentiating human induced pluripotent stem cells (hiPSCs) into three-dimensional retinal tissue comprising functional photoreceptors, the method comprising the steps of (a) on day 0 of differentiation, (i) enzymatically detaching hiPSCs cultured on Matrigel-coated plates with mTeSR™ 1 medium, and (ii) culturing the hiPSCs in suspension to induce formation of aggregates; (b) during days 1-3 of differentiation, transitioning the aggregates into neural induction medium (NIM); (c) seeding the aggregates on to Matrigel-coated dishes on day 7; (d) on day 16, replacing NIM with a chemically-defined differentiation medium; and (e) on the fourth week of differentiation, (i) detaching neural retina (NR) domains, and (ii) culturing in suspension; (f) at any time between day 30 and 42, adding fetal bovine serum to promote cell survival; (g) adding 1 µM all-trans retinoic acid on day 63, to induce photoreceptor maturation; and (h) decreasing the concentration of all-trans retinoic acid to 0.5 µM at any time between day 90 and day 98. The present invention also provides the three-dimensional retinal tissue produced by such method.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Figure 5:
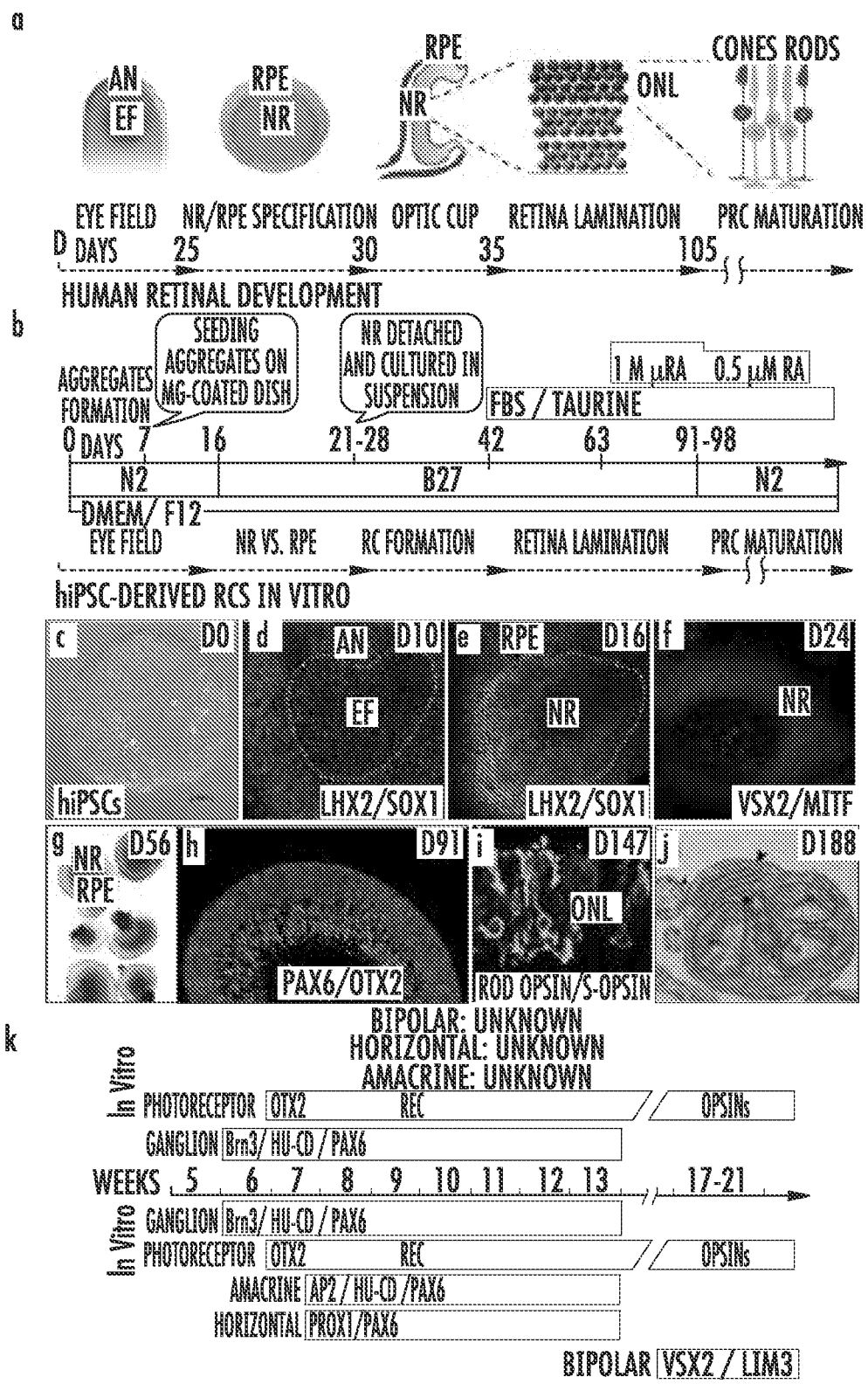
FIG. 5. Retinogenesis during human embryonic development and in 3-D retinal cups (RCs) derived from hiPSCs. a, Main steps leading to the formation of the human retina in vivo. b, Diagram of the optimized culture conditions used for inducing hiPSCs to recapitulate retinogenesis in vitro. c-j, Main steps of RC development in vitro: hiPSCs (c) differentiated into retinal progenitors that self-organized into eye field-like domains (EF, d) which subsequently differentiated into a central neural retina (NR) domain and a peripheral RPE domain (e). As differentiation progressed, the NR domain acquired an optic-cup-like shape (f) and formed a 3D-RC when cultured in suspension (g). Over time, RCs acquired the characteristic retinal lamination (h), including a well-organized outer nuclear layer (ONL) containing highly mature rod and cone photoreceptors showing expression of the corresponding opsins (i) and formation of outer-segment discs (demarcated by arrowheads, j). k, Timeline of retinal neurogenesis in 3D-RCs in vitro compared to in vivo human retina.

Retinal development occurs within a very dynamic and complex microenvironment involving highly-coordinated cell-cell interactions through direct contact or diffusible signals[7,8]. Accordingly, in published studies so far, the differentiation of ES or iPS cells into retinal cells in vitro typically required an elaborate regime of exogenous factors[5,6,9-14]. Here, we succeeded in inducing the differentiation of hiPSCs into retinal progenitors that self-organized into a 3-dimensional retinal cup with a simple procedure, involving just a few factors to promote cell survival and photoreceptor maturation (FIG. 5). Most importantly, the photoreceptors in our preparations were able to reach the stage of photosensitivity.

Figure 1:
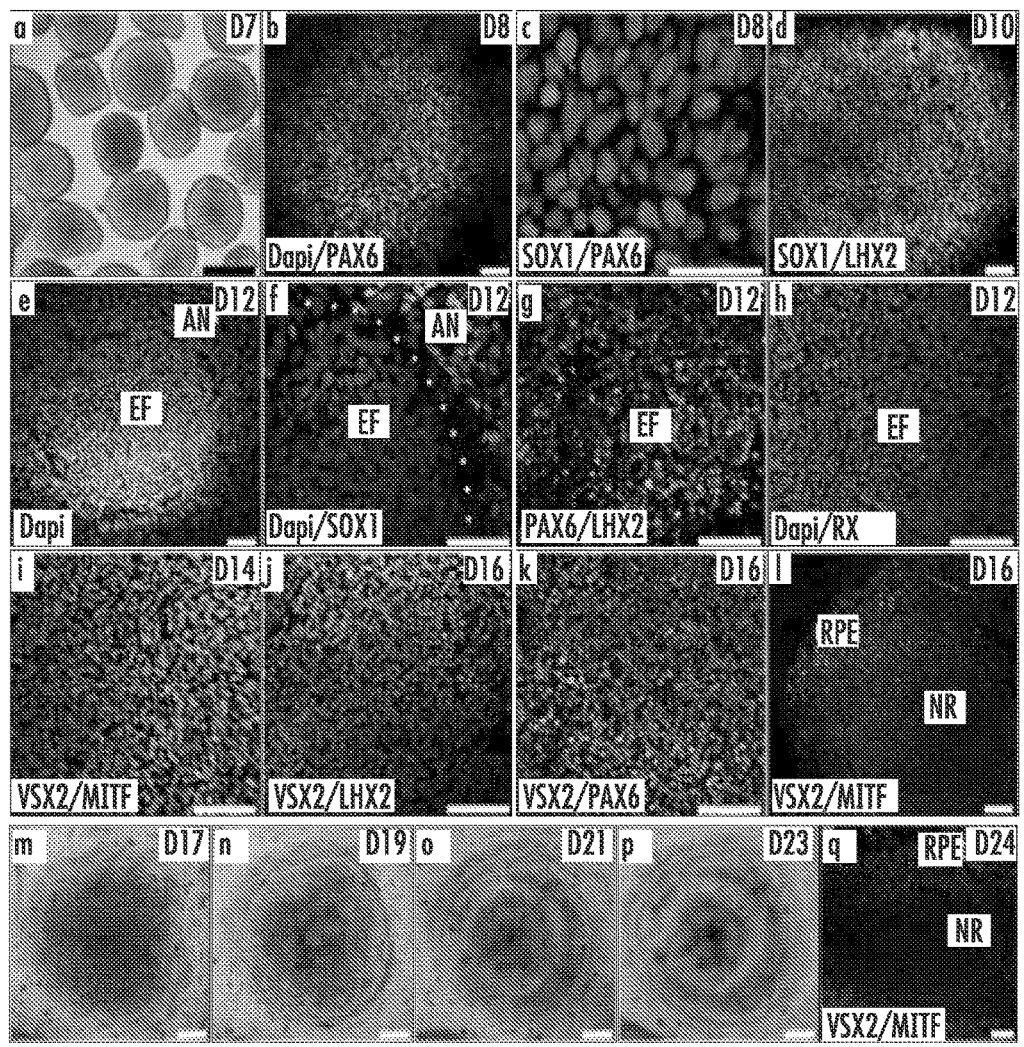
FIG. 1. hiPSC-derived retinal progenitors self-organized into eye field-like domains (EF) and subsequently differentiated into neural retina (NR) and retinal pigment epithelium (RPE). a-d, hiPSC-derived, free-floating aggregates (a) seeded in matrigel-coated dishes acquired an anterior neuroepithelial (AN) fate characterized by SOX1/PAX6 expression (b-c); subsequently, the first retinal progenitors (LHX2-positive) appeared in the center of the aggregates (d). e-h, By D12, well-defined EF domains (e,f) expressing PAX6, LHX2 and RX (g,h) could be observed surrounded by AN cells (f). i-l, As differentiation progressed, cells within the EF domains co-expressed VSX2 and MITF (i), and afterward differentiated into a central VSX2/LHX2/PAX6-positive NR domain (j-l) and a peripheral RPE domain expressing MITF but not VSX2 (l). m-q, These NR domains progressively acquired an optic-cup-like shape. r, Efficiency of NR-domain formation among three hiPSC lines (mean±SD, 3 experiments/cell line). s, RT-PCR analysis showing progressive acquisition of retinal fate. Scale bars: 200 μm (a and m-p); 50 μm (b,d,e,l,c,f-k, and q).
Figure 6:
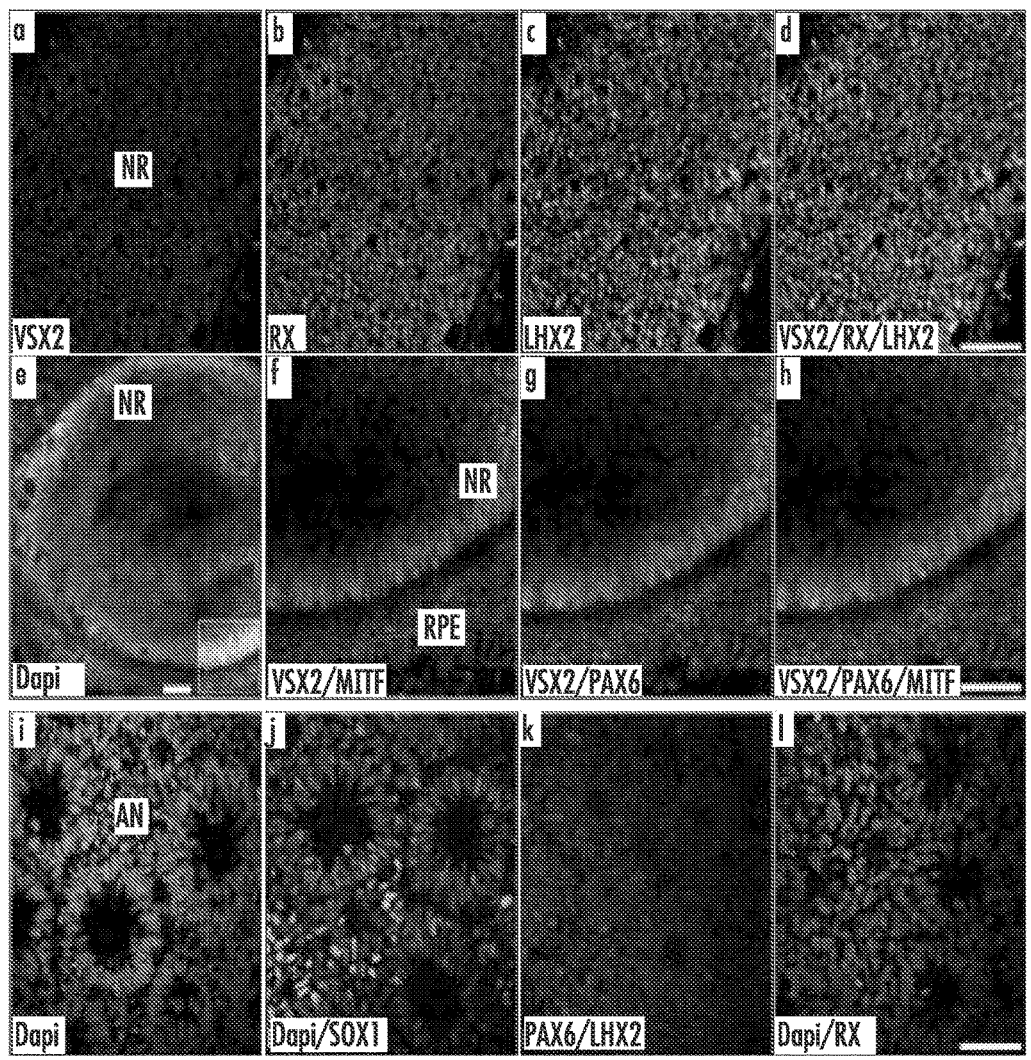
FIG. 6. Coexisting cellular domains in D16 to D28 cultures. Cell differentiation in these cultures is not synchronized; therefore, in a given culture dish, early neural retina (NR) domains (a-d), optic cup-like NR and surrounding retinal pigment epithelium (RPE) domains (e-h) and anterior neuroepithelial (AN) cells forming characteristic rosettes (i-l) were found simultaneously. Scale bars: 50 μm.

Eye development in the embryo's neural plate begins with the formation of the eye field (EF), a centrally-organized domain consisting of a subpopulation of anterior neuroepithelial cells that have become further specified into retinal progenitors' (FIG. 5a). The EF is characterized by the expression of a group of transcription factors including PAX6, RX, LHX2, SIX3, and SIX6, while the surrounding anterior neuroepithelial cells express PAX6 and SOX1[15-17]. In parallel to the native events, our hiPSC-derived aggregates, after 8 days of differentiation (D8) in a chemically-defined neural-differentiation medium and attached on Matrigel-coated culture dishes, acquired an anterior-neuroepithelial fate expressing PAX6 and SOX1 (FIG. 1a-c). Soon after, retinal progenitor cells expressing LHX2 appeared in the central region of the differentiating aggregates (FIG. 1d). By D12, well-defined EF-like domains expressing the appropriate transcription factors could be observed (FIG. 1e-h) surrounded by anterior-neuroepithelium-like cells (FIG. 1f). These anterior-neuroepithelium-like cells typically formed rosettes (FIG. 6i-1), which although not found in the native situation, are characteristic of these cells in culture[18].

The RT-PCR analyses in FIG. 1s summarize the temporal sequence of events in culture, showing the gradual loss of the hiPSCs' pluripotency (loss of OCT4), the acquisition of neural fate (sustained SOX2 expression, and appearance of PAX6), and the progressive differentiation into retinal progenitors. The chronology of expression of the eye-field transcription factors mimicked the in vivo situation, with initial expression of PAX6 and SIX3, then LHX2 and RX, and eventually SIX6[15]. Thus, without exposure to any "retinalizing" exogenous factors, hiPSCs were still able to differentiate into retinal progenitors that self-organized into EF-like domains surrounded by anterior neuropepitheliallike cells, presenting a cellular organization closely resembling the embryonic anterior neural plate where the EF forms in vivo.

The EF in vivo gives rise to the left and right optic vesicles, with their respective retinal progenitors eventually forming the future neural retina (NR) and retinal pigment epithelium (RPE) (FIG. 5a). Cell-fate specification into either NR or RPE is regulated critically by two transcription factors, VSX2 and MITF, which initially are co-expressed in the bipotential progenitor cells but subsequently become restricted to the NR and RPE, respectively[7,19,20]. Again, as in the native situation, the cells within the EF-like domains in our cultures followed the same differentiation sequence; namely, these cells initially expressed both VSX2 and MITF (FIG. 1i), but subsequently segregated into a central NR-like domain expressing PAX6, LHX2, RX and VSX2 (FIG. 1j-1; FIG. 6a-d), and a peripheral RPE-like domain expressing MITF and PAX6 (FIG. 1l and FIG. 5e). Between D17 and D25 in culture, these NR and RPE domains transitioned to an optic-cup-like structure, with the NR progressively acquiring a horseshoe-dome shape reminiscent of the inner wall of the optic cup, surrounded by the RPE (FIG. 1m-q; FIGS. 5f and 2e-h).

Similar results were obtained from three different hiPSC lines, with the efficiency of NR-domain formation in D20 being 85.0±3.0%, 88.34±3.5% and 62.3±4.6%, respectively (mean±SD) (FIG. 1r). Thus, in our cultures, retinal progenitors in the EF domains underwent spontaneous differentiation into NR and RPE efficiently and reproducibly, closely mimicking their in vivo topological organization in the correct temporal sequence.

Figure 2:
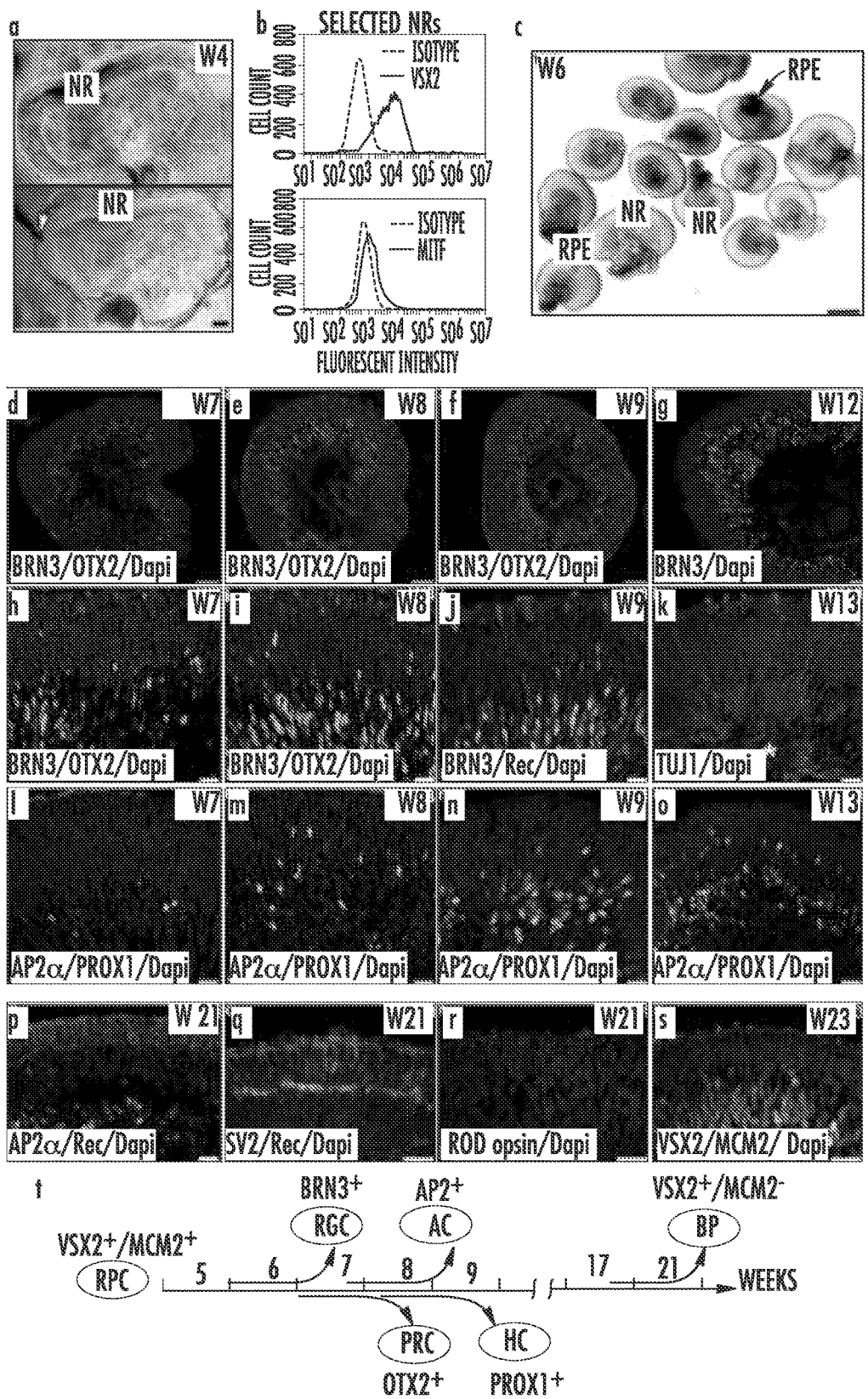
FIG. 2. hiPSC-derived neural retina (NR) progenitors formed 3-D retinal cups and recapitulated the spatiotemporal pattern of NR differentiation in vivo. a, One NR domain (top panel) is being detached with a tungsten needle (arrowhead in bottom panel). b, FACS analysis of collected NR domains showed enrichment in NR progenitors (VSX2-positive) compared to RPE progenitors (MITF-positive). c, Detached NR domains cultured in suspension formed 3-D retinal cups (RCs), each composed of a NR epithelium and RPE bundled at the tip. d-o, Cells within the RCs differentiated and migrated to their corresponding layers, with ganglion cells (BRN3-positive, d-j; TUJ1-positive, k where (*) indicates a developing nerve-fiber-like layer) appearing first, followed by photoreceptors (OTX2/recoverin-positive, d-f, h-j), amacrine cells (AP2α-positive, l-o), and horizontal cells (PROX1-positive, l-o). p-s, By W23, RCs presented a well-established outer nuclear layer (Recoverin-positive, p-q) delineated by a developing outer plexiform layer (SV2-positive, q) and containing rod-opsin-positive photoreceptors (r), and a developing bipolar cell layer (s) containing bipolar cells (VSX2-positive/MCM2-negative) intermingled with remaining progenitor cells (VSX2-positive/MCM2-positive). t, Timeline of retinogenesis in 3D-RCs. Scale bars: 100 μm (a, c, and d-f); 20 μm (g, h-p, and q-s).
Figure 7:
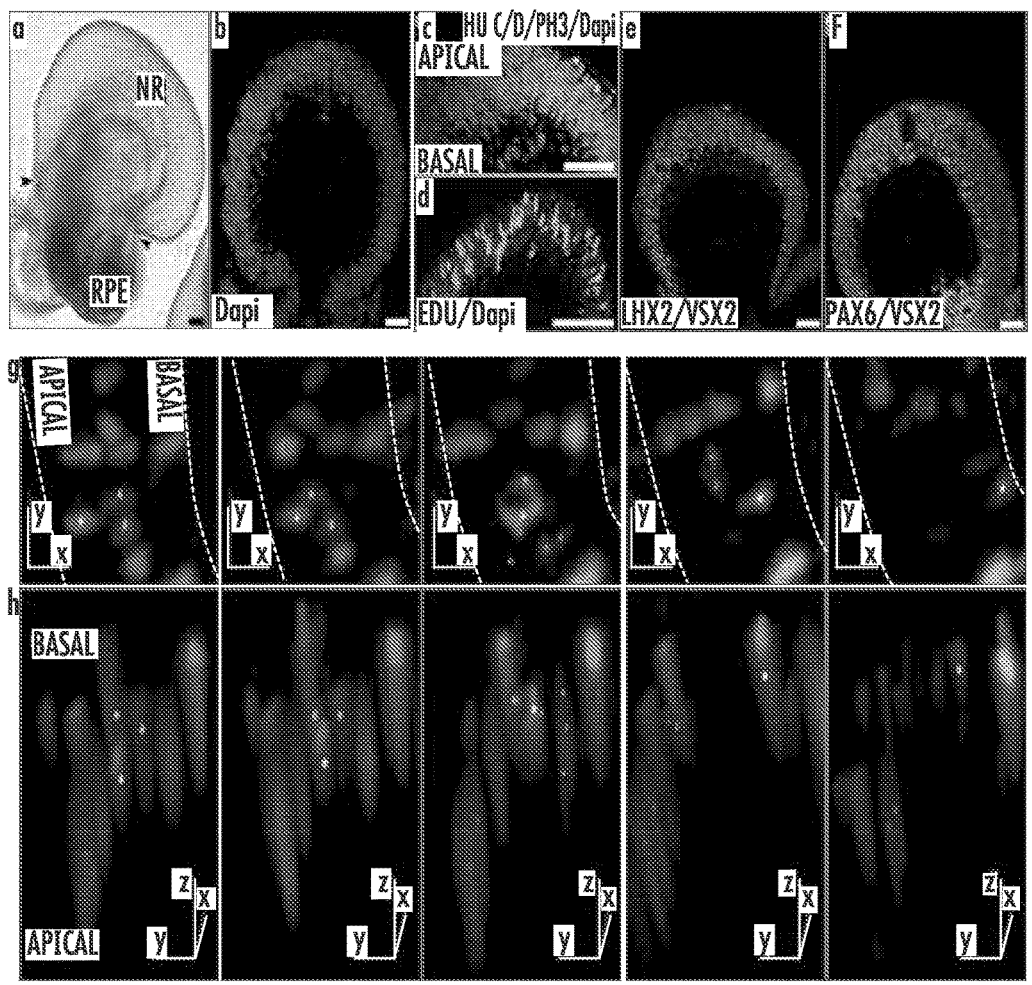
FIG. 7. Features of the neural retina (NR) epithelium within hiPSC-derived retinal cups (RCs). a, RCs were composed of a NR epithelium continuous with the adjacent RPE bundled at the tip (arrowheads). b-c, The pseudostratified neural epithelium within the RC showed the typical polarity, with mitosis (PH3-positive) occurring at the apical side, and postmitotic neuronal precursors (HU C/D-positive) accumulating at the basal side. d-f, NR cells proliferated actively (EdU-positive, d) and co-expressed transcription factors characteristic of neural retina progenitor cells (e-f). g-h, Retinal progenitors within the NR epithelium underwent interkinetic nuclear migration. g, Time-lapse imaging of retinal progenitors expressing nuclear GFP. h, 3-D volume rendering of the cells shown in (g). red dot: cell undergoing mitosis; yellow dot: cell nucleus migrating from the apical to the basal side of the neuroepithelium; blue dots: cells undergoing apoptosis. Scale bars: 50 μm.
Figure 8:
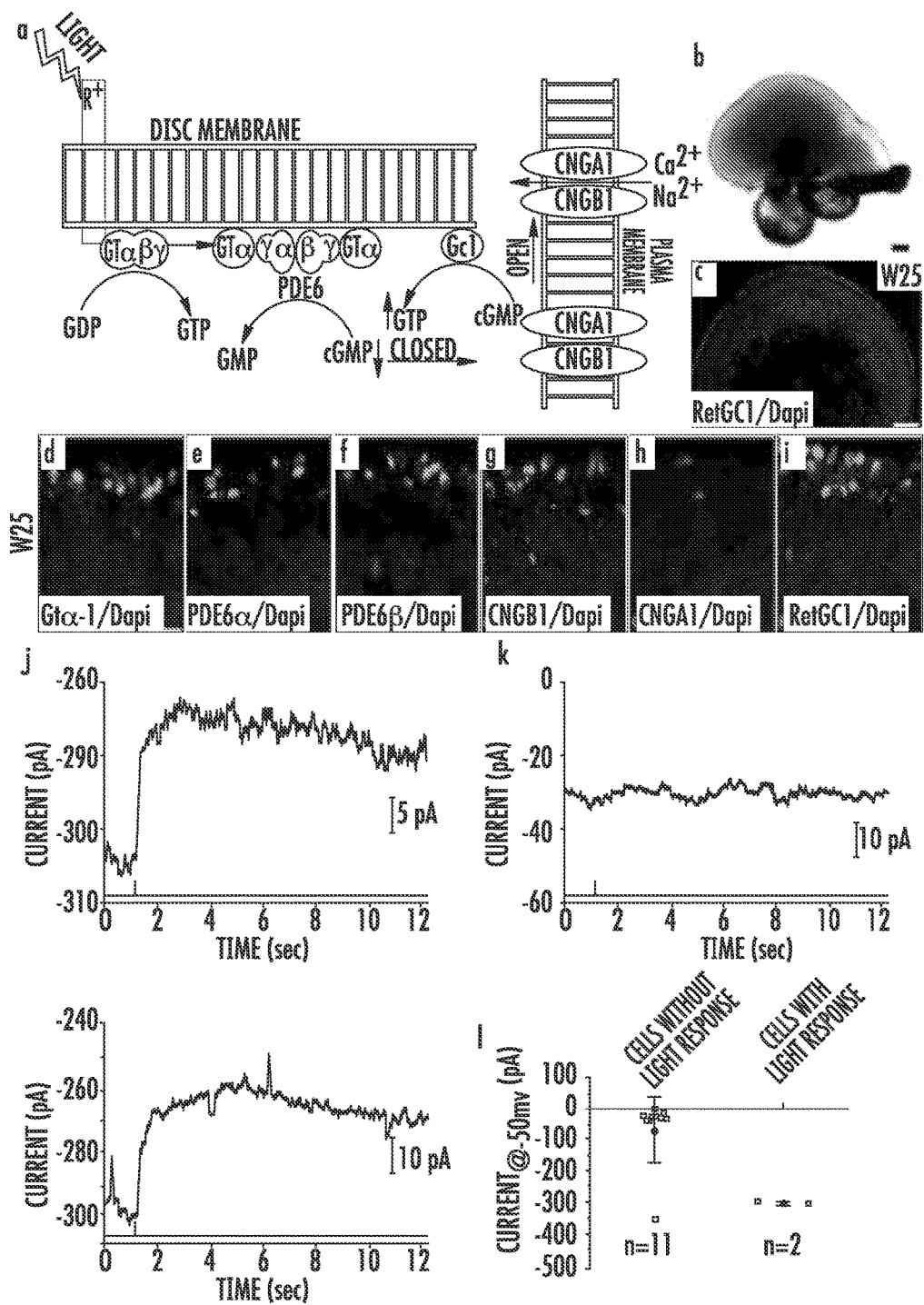
FIG. 8. Retinal progenitors within hiPSC-derived retinal cups underwent spontaneous differentiation. Retinal progenitors differentiated following the typical central-to-peripheral pattern (a-c) and acquired early-born cell fates, beginning with generation of ganglion cells (BRN3-positive/EdU-negative, d-f), followed by photoreceptors (OTX2-positive, f), amacrine cells (AP2α-positive, g) and horizontal cells (AP2α/PROX1-positive, arrows in g). Scale bars: 50 µm.
Figure 9:
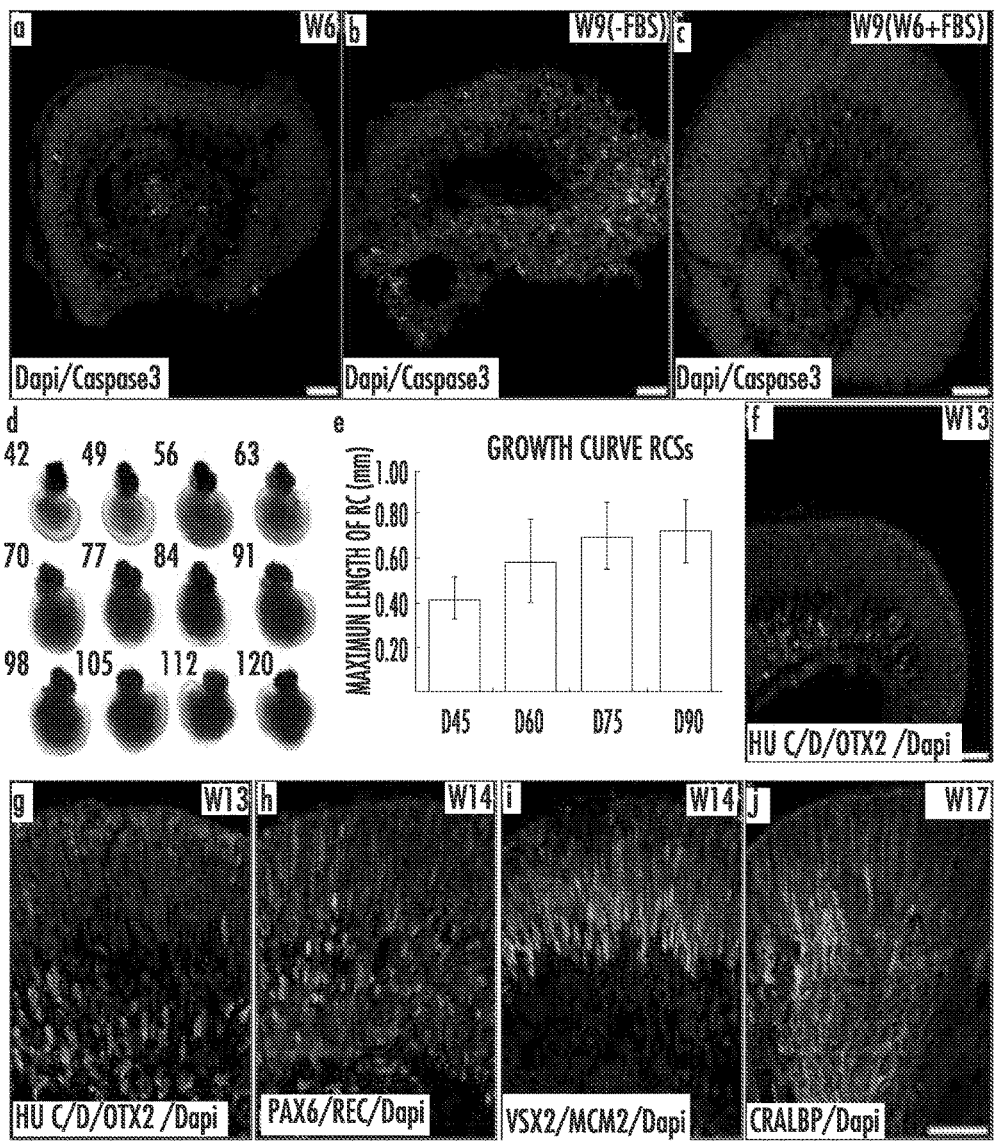
FIG. 9. Long-term suspension culture of hiPSC-derived retinal cups (RCs). a-c, After W7, RCs progressively lost their histological organization due to increasing cell death (caspase 3-positive, a-b), which was avoidable by supplementation with FBS, taurine and retinoic acid from the beginning of W7 onward (c). d-e, Under these conditions, RCs maintained their shape, cellular organization, and steady growth during long-term culture (bars: mean±SD). f-i, By W13-14, RCs showed distinguishable layers containing the precursors of most of the major neuronal cell types, including ganglion, amacrine and horizontal cells (HU- and PAX6-positive), and photoreceptors (OTX2- and recoverin-positive); as in the developing human retina, cells expressing OTX2 and recoverin were observed in the developing outer nuclear layer as well as in the inner side of the retinal epithelium[35,36]. A conspicuous neuroblastic layer containing mitotic retinal progenitors (VSX2/MCM2-positive) was still present by W14 (i). j, Müller cells expressing CRALBP were first seen by W17. Scale bars: 50 µm.

The optic-cup-like shape of the NR domains in our cultures made them easily identifiable and amenable to mechanical detachment one by one, and collection for further culture in suspension (FIG. 2a). The NR domains, collected in D21-D28, had a high enrichment of NR progenitors (71.0±7.3% VSX2-positive cells vs. 19.0±7.2% MITF-positive cells, mean±SD; FIG. 2b) and, when cultured in suspension, formed 3-D retinal cups (FIG. 2c) with an efficiency ranging from 50% to 70% (estimated from over 100 NR domains/experiment and 3 independent experiments), depending on the level of stringency at the time of NR collection. The retinal cup comprised a thick, transparent NR continuous with the adjacent RPE, which appeared bundled at the tip of the retinal cup and became gradually pigmented (FIG. 7a). From the time of NR-domain collection to D35 (Week 5, or W5), the NR presented molecular and histological features resembling the actual features of the human embryonic retina at the same age[21], including a polarized, pseudostratified epithelium with proliferating cells undergoing interkinetic nuclear migration and expressing the appropriate transcription factors (FIG. 7). During W5-W7, the NR cells spontaneously began to differentiate, following the characteristic center-to-periphery wave of neurogenesis and migrating to their corresponding retinal layers (FIG. 8).

In order to promote cell survival beyond W7, the culture medium had to be supplemented with fetal bovine serum (FBS), taurine and retinoic acid until W17, at which time further slight modifications (less retinoic acid and replacement of the neurobasal supplement B27 by N2) were made to induce photoreceptor maturation. These conditions allowed the retinal cups to maintain their shape and steady growth (longest axis increasing from 0.4±0.1 mm on D45 to 0.7±0.1 mm on D90, mean±SD) (FIG. 9a-e) and develop distinguishable layers containing all major retinal cell types, including Müller cells (FIG. 9f-j). Ganglion cells first appeared in W5 (FIG. 8d) and over time increased in number and migrated toward the emerging ganglion cell layer (FIG. 2d-j), which became well-established by W12-13 (FIG. 2g), sometimes including a developing nerve-fiber-like layer (FIG. 2k). Photoreceptors (expressing OTX2) appeared during W7 and, over the subsequent weeks, populated the developing outer nuclear layer (where photoreceptor cell bodies are situated in the mature retina) and expressed recoverin, a well-known phototransduction protein (FIG. 2d-f and h-j). Amacrine cells (expressing AP2α) and horizontal cells (expressing PROX1) also appeared during W7 (FIG. 2l). As time progressed, amacrine and horizontal cells became numerous, and began to segregate to their corresponding layers (FIG. 2m-o). By W21, the retinal cups presented a well-organized outer nuclear layer, adjoining a developing outer plexiform layer expressing the synaptic-vesicle protein, SV2 (FIG. 2p-q). Rod opsin was also detectable in the distal part of photoreceptor cells (FIG. 2r). Finally, a developing bipolar cell layer containing postmitotic, VSX2-expressing bipolar cells appeared after W22 (FIG. 2s). This spatiotemporal pattern of differentiation closely mimics that of the native retina[22,23] and was observed in all the retinal cups examined (~60) derived from the three different hiPSC lines we used (FIG. 2t and FIG. 5k).

Figure 3:
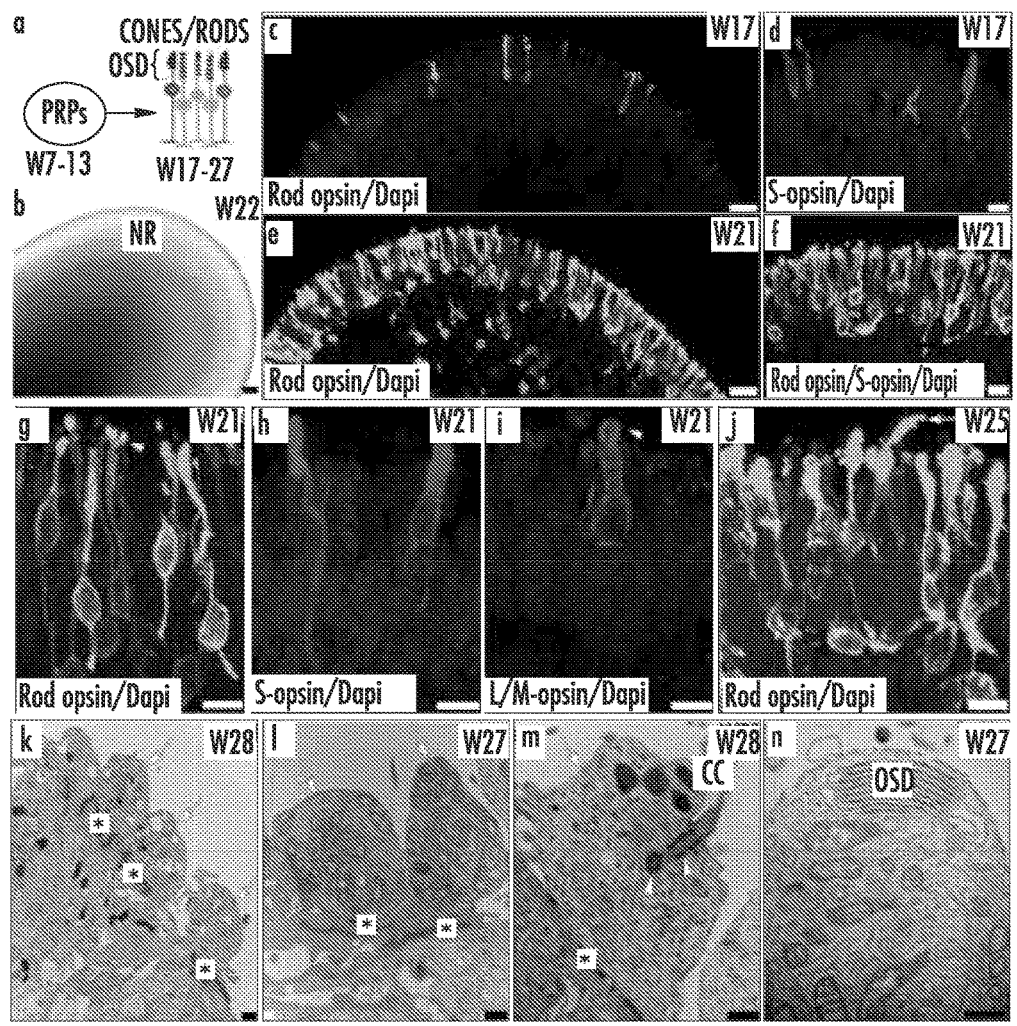
FIG. 3. hiPSC-derived rod and cone photoreceptors achieved an advanced level of differentiation including outer-segment disc formation. a, During normal development photoreceptor precursors (PRPs) differentiate into rods, L/M-, and S-cones (green, red and blue color respectively). b, A W22 retinal cup that has been exposed to 1 μM retinoic acid in W10-W14. c-j, Under these conditions, photoreceptors expressing high levels of rod-opsin in the entire cell body were first observed by W17 (c), significantly increasing in number and forming large patches by W21 (e-f). S-opsin expression could be observed in some rod-opsin-negative photoreceptors (d,f). High-magnification images of W21 retinal cups showing rods (g), S-(h) and L/M-(i) cones with a morphology and a topological organization similar to those of in vivo retina, including structures reminiscent of short, nascent outer segments (arrowheads). By W25, elongated structures resembling more developed outer segments were observed (j, arrow). k-n, Transmission-EM analysis revealed the presence of an outer limiting membrane (*), inner segments (arrows), basal bodies (arrowheads, k), connecting cilia (CC) and outer segment discs (OSD). Scale bars: 50 μm (a, b, and d); 10 μm (c and e-i); 0.5 μm (j-m).
Figure 4:
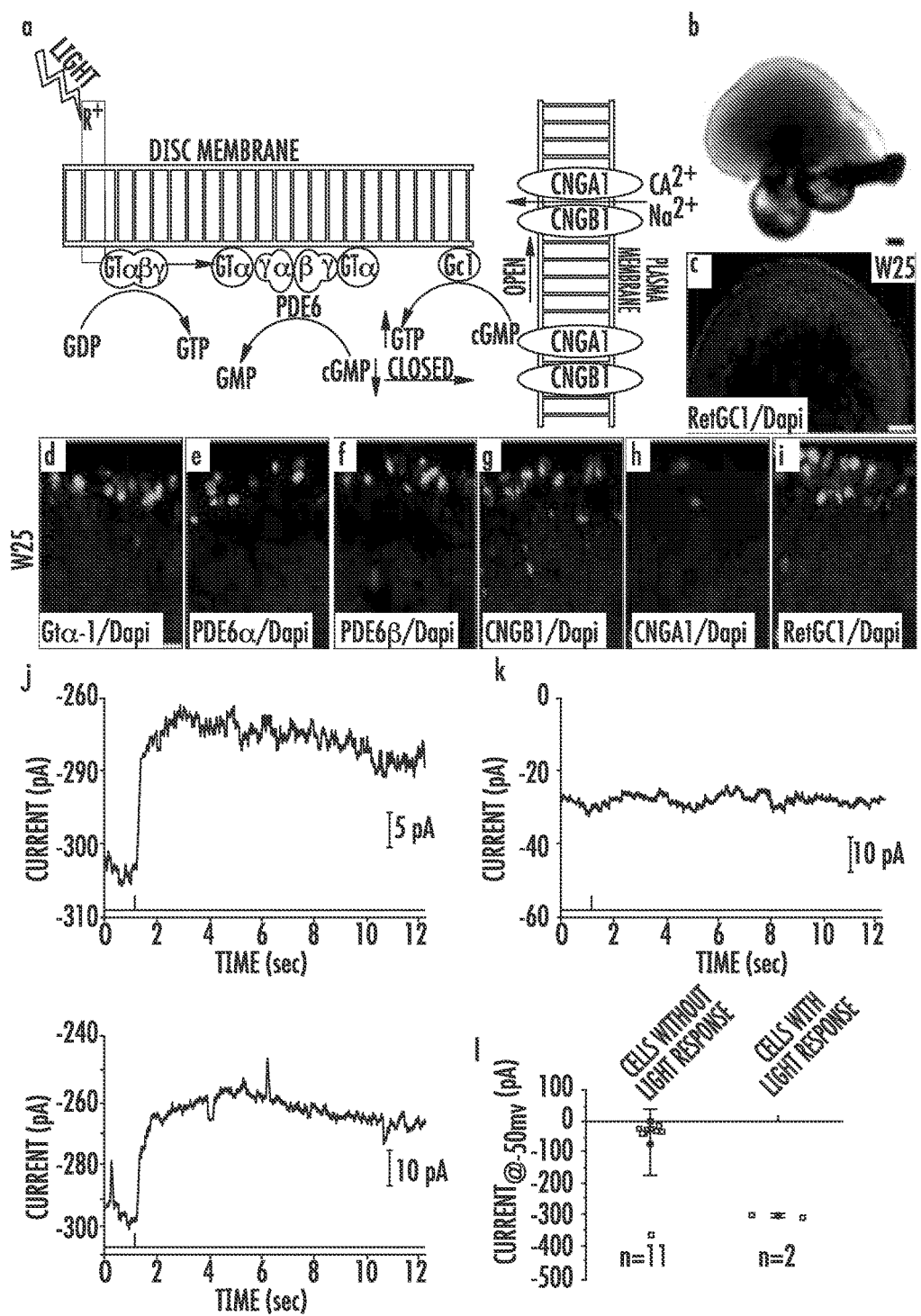
FIG. 4. hiPSC-derived photoreceptors expressed proteins of the phototransduction pathway and occasionally showed light response in vitro. a, Diagram of rod phototransduction pathway in vivo. b, 3-D retinal cups (RCs) still maintained their structural organization in W27. c-i, Photoreceptors within the RCs showed expression of phototransduction proteins with the appropriate cellular distributions. j-l, Perforated-patch electrophysiological recordings from RC photoreceptors, showing the flash-triggered responses (single trial) from two light-sensitive cells (j), the lack of flash response from one light-insensitive cell (k), and collected data from 13 cells (l). Cells were voltage-clamped at −50 mV. Inward current is negative. Flash (indicated by arrow) was 40 ms in duration and 2.46×10$^5$ μW cm$^{-2}$ in intensity (white light from a mercury arc lamp). In panel 1, open circles indicate individual cells, solid circles indicate mean values, and error bars indicate SD. Scale bars: 50 μm (b and c); 5 μm (d-i).
Figure 10:
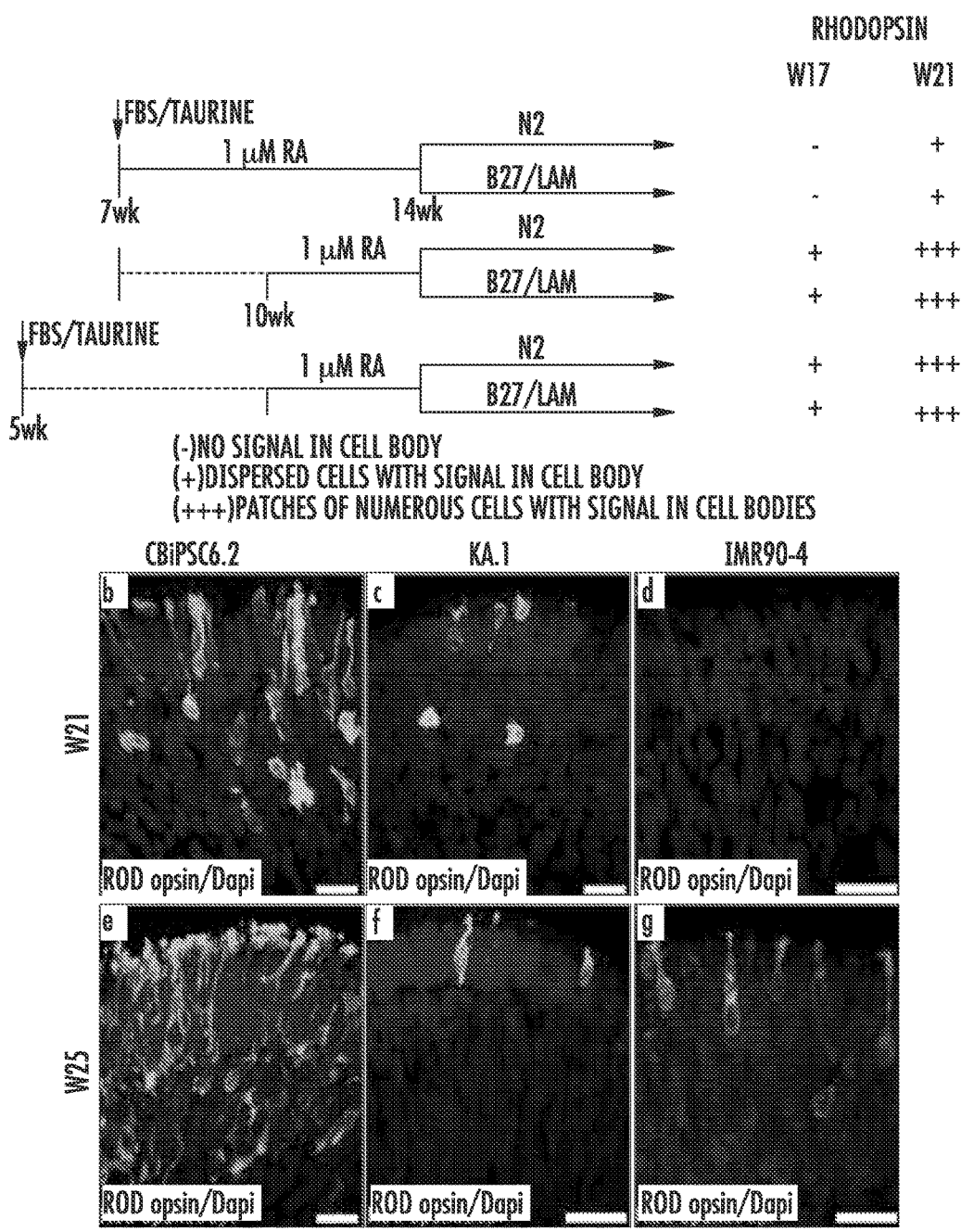
FIG. 10. Effect of retinoic acid on the differentiation of hiPSC-derived photoreceptors. a, Two windows of exposure to 1 µM retinoic acid (RA) were tested in combination with slight modifications to the culture media in CB-iPSC6.2-derived retinal cups (RCs). RA treatment in W7-W14 lead to low levels of rod-opsin expression in the distal part of photoreceptor cells as observed in the original culture conditions, except for some RCs that showed few cells with rod-opsin expression in the cell bodies at W21. In contrast, RCs treated during W10-W14 showed dispersed cells with strong rod-opsin expression in their cell bodies already at W17, and forming large patches at W21. We did not observe significant differences associated with modifications of the culture media after RA treatment or presence of FBS/Taurine from W5. Similar results were observed in 3 independent experiments. b-g, When KA.1- and IMR90-4-derived RCs were subjected to RA treatment in W10-W14, induction of rod-opsin expression was also observed, although at a later time and less efficiently than in CB-iPSC6.2-derived RCs. In all cases, rod-opsin expression was evaluated qualitatively by microscopic observation. Scale bars: 20 µm.
Figure 11:
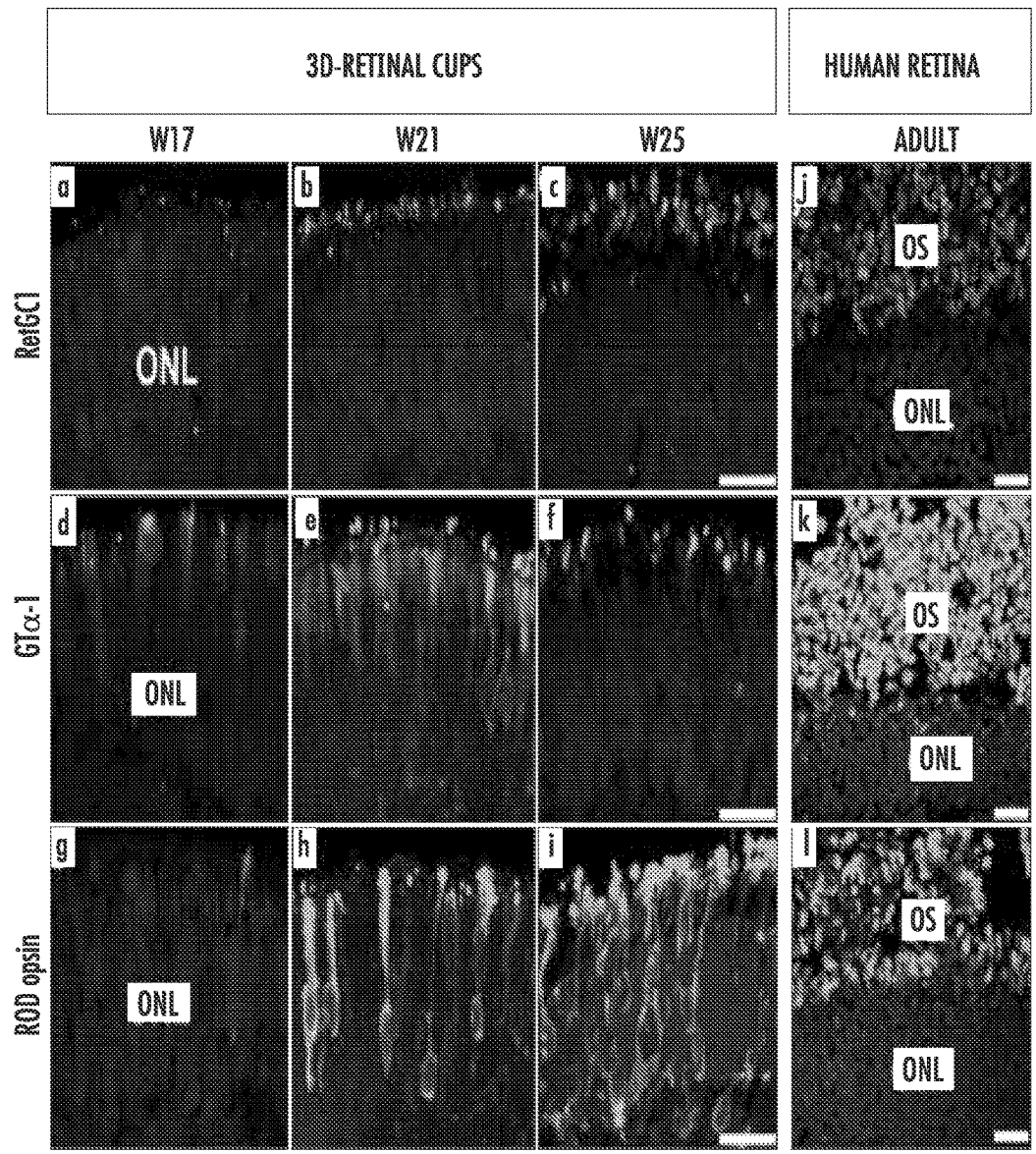
FIG. 11. hiPSC-derived photoreceptors within the retinal cups (RCs) gradually acquired expression of proteins involved in phototransduction. a-i, As observed in the developing human retina in vivo[26], expression of the phototransduction proteins increased in parallel to that of rhodopsin. j-l, Antibodies used for detecting proteins associated with the phototransduction pathway in the RCs were validated in adult human retina as shown in these examples. Scale bars: 50 µm (b and c); 10 µm (d-i).

In the above culture conditions, although the photoreceptors expressed detectable levels of rod opsin, they did not appear to continue maturing, such as forming outer-segment discs. At the same time, no expression of L/M- and S-cone opsins was apparent. Because retinoic acid has been shown to influence photoreceptor differentiation in a time- and concentration-dependent manner[24,25], we reasoned that prolonged exposure to a relatively high retinoic-acid concentration (1 μM retinoic acid in W7-W17) might hamper photoreceptor maturation. Accordingly, we tried two shorter time windows of retinoic-acid exposure (W7-W14 and W10-W14, both with 1 μM retinoic acid; FIG. 10). The W10-W14 condition showed, already at W17, dispersed cells with higher rod-opsin expression, not just in the distal part of the immature photoreceptors but also in their cell bodies, as in native development[26] (observed in ~50% of the retinal cups, n=8; rod-opsin expression remained weak in the remainder) (FIG. 3a-c). Moreover, we began to observe S-opsin expression in some photoreceptors not expressing rod opsin (FIG. 3d). By W21, 90% of the retinal cups (n=20) showed a significant increase in the number of photoreceptors expressing rod opsin, organized in patches throughout the outer nuclear layer or even encompassing the full extent of this layer (FIG. 3e). Photoreceptors expressing L/M- or S-opsins were also observed (FIG. 3f). The morphologies of the rods and cones and the localization of their cell bodies, with cones at the outer edge and rods toward the inner edge of the outer nuclear layer, resembled remarkably the native situation[26] (FIG. 3g-j). The photoreceptors showed rounded structures at their distal tip reminiscent of the short nascent outer segments at comparable developmental stages in the human retina[26] (FIG. 3 g-i arrowheads). Although infrequent, there were also elongated structures resembling more advanced native outer segments in W25 (FIG. 3j, arrow).

During W27-W28, several ultrastructural features of functional significance appeared in electron microscopy, including an outer limiting membrane, inner segments with numerous mitochondria, basal bodies, and connecting cilia (FIG. 3k-m). Although at low frequency, some photoreceptors also showed intracellular membrane discs reminiscent of the outer-segment discs in mature photoreceptors (FIG. 3n and FIG. 5j). All of these features were very similar to those observed in the human developing retina in vivo[27,28].

Perhaps most importantly, based on immunocytochemistry with specific antibodies verified in adult human retina (FIG. 11j-l), several key proteins involved in rod phototransduction were expressed in the photoreceptors of W25 retinal cups, including the a-subunit of rod transducin ($G_{T1\alpha}$), the $\alpha$- and $\beta$-subunits of the rod cGMP-phosphodiesterase ($PDE6_{\alpha\beta}$), the rod cyclic-nucleotide-gated-channel a-subunit (CNGA1) and $\beta$-subunit (CNGB1), and retinal guanylate cyclase 1 (RetGC1) (FIG. 4a-i). These proteins increased in expression over time in parallel to rod opsin, as in native human retina[26] (FIG. 11a-i). With perforated-patch recordings in the voltage-clamp mode from the rod-like cells in W25-W27 RCs, we found 2 out of 13 randomly chosen cells to respond to a light flash (FIG. 4j). This response consisted of the suppression of a standing dark inward current, similar to the situation in native rods; the speed of the response's rising phase also resembled that of the native response. The photosensitivities of the two responsive cells were much lower than normal, likely because the rhodopsin level was still low and the downstream phototransduction steps still maturing; repeated flashes also failed to elicit further responses. Possibly for the same reasons, light did not completely suppress the dark inward current (see also Reference 29 for a cGMP-induced current in their preparations). Because of the very low incidence of W27 photoreceptors with visible outer-segment discs in the retinal cups used for recordings, we consider the percentage of responsive cells encountered to be actually very respectable. Finally, and with interesting correlation, almost all light-insensitive cells recorded had a much smaller dark inward current (FIG. 4k, l). Compared to the progressive maturation of photoreceptors, most ganglion cells and amacrine cells, on the other hand, gradually disappeared from the advanced cultures, presumably because they needed additional factors for their long-term survival.

In summary, we have developed a simple and highly-efficient strategy for inducing hiPSCs to differentiate, almost autonomously, into 3-dimensional retinal tissue in vitro, with spatial and temporal features that replicate the development of the human retina in vivo. The photoreceptors in our system are able to reach an advanced stage of maturation, up to at least the beginning of outer-segment formation and of photosensitivity. To our knowledge, this is the first time that such a developmental step has been achieved in vitro. Surprisingly, this degree of photoreceptor maturation does not require physical contact with the RPE, which may have important implications about the intrinsic developmental program in these cells. Finally, the success here with human iPSCs obviously opens up many exciting possibilities in establishing models for human eye diseases, and hopefully will also take potential therapeutic applications one step closer to reality.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

The following describes one embodiment of the present invention. On day 0 (D0) of differentiation, human iPSCs cultured on Matrigel-coated plates with mTeSR1 medium, were enzymatically detached by dispase treatment and cultured in suspension to induce formation of aggregates. During the following three days, aggregates were gradually transitioned into neural induction medium (NIM), and seeded onto Matrigel-coated dishes on D6-7. On D16, NIM was replaced by a chemically-defined differentiation medium containing DMEM/F12 (3:1), 2% B27 (without vitamin A, Invitrogen), 1× minimum essential media-non essential amino acids (NEAA), and 1% antibiotic-antimycotic (Gibco). On the 4$^{th}$ week of differentiation (D22-28), horseshoe-shaped neural retina (NR) domains were manually detached and cultured in suspension, where 3-dimensional retinal cups gradually formed. On D42, the medium was supplemented with 10% fetal bovine serum (FBS; Gibco), 100 µM Taurine (Sigma) and 2 mM GlutaMAX (Invitrogen) to promote cell survival. To induce photoreceptor maturation, all-trans retinoic acid (RA; Sigma) was added daily to a final concentration of 1 µM from D63 to D91-98, and decreased to 0.5 µM thereafter.

hiPSC Culture.

Three hiPSC lines, IMR90-4 (WiCell), CB-iPSC6.2 and KA.1, were used in this study (Table 1). All cell lines were obtained with verified normal karyotype and contamination-free. hiPSCs were maintained on Matrigel (growth-factor-reduced; BD Biosciences) coated plates with mTeSR1 medium (Stemcell Technologies) according to WiCell protocols. Cells were passaged every 5-7 days at approximately 80% confluence. Colonies containing clearly visible differentiated cells were marked and mechanically removed before passaging. The use of human iPS cells in this study conforms to The Johns Hopkins Institutional Stem Cell Research Oversight (ISCRO) Committee.

TABLE 1

Human iPS cell lines used in this study.

| Cell Line | Cell of Origin | Reprogramming Method | Genomic Integration | Ref |
|---|---|---|---|---|
| CB-iPSC6.2 | Human CD34+ cord blood-derived myeloid progenitors | non-viral 7-factor episomes (SOX2, OCT4, KLF4, MYC, NANOG, LIN28, SV40T) with BMSC-priming of myeloid donors | NO | 17 |
| KA.1 | Human adult keratinocytes | non-viral 7-factor episomes (SOX2, OCT4, KLF4, MYC, NANOG, LIN28, SV40T) | NO | 18, 29 |
| IMR90-4 | Human fibroblast cell line IMR90 | Lentiviral 4 factors (SOX2, OCT4, NANOG, LIN28) | YES | 34 |

Three human iPS cell lines of different cell origin and reprogramming method where chosen in order to test the reproducibility of our method across cell lines.

Early Stages of Retinal Differentiation.

The procedure to induce early stages of retinal differentiation was based on a previously described protocol with major modifications[29,30]. Briefly, on day 0 (D0) of differentiation, hiPSCs were enzymatically detached by dispase treatment, dissociated into small clumps, and cultured in suspension with mTeSR1 medium and 10 μm Blebbistatin (Sigma) to induce aggregate formation. Aggregates were gradually transitioned into neural-induction medium (NIM) containing Dulbecco's modified eagle medium (DMEM)/F12 (1:1), 1% N2 supplement (Invitrogen), 1× minimum essential media-non essential amino acids (NEAA), 2 μg ml$^{-1}$ heparin (Sigma), by replacing the medium with a 3:1 ratio of mTeSR1/NIM on D1, 1:1 on D2, and 100% NIM on D3. On D6-7 aggregates were seeded onto Matrigel-coated dishes containing NIM, and switched to DMEM/F12 (3:1) supplemented with 2% B27 (without vitamin A, Invitrogen), lx NEAA, and 1% antibiotic-antimycotic (Gibco) on D16. Thereafter, the medium was changed daily.

Formation of 3-D Retinal Cups.

On the 4$^{th}$ week of differentiation (D22-28), horseshoe-shaped neural retina (NR) domains were manually detached with a sharpened Tungsten needle under inverted microscope, collected and cultured in suspension at 37° C. in a humidified 5% CO$_2$ incubator in DMEM/F12 (3:1) supplemented with 2% B27, lx NEAA, and 1% antibiotic-antimycotic where they gradually formed 3-dimensional retinal cups (RCs). Thereafter, the medium was changed twice a week. For long-term suspension culture, the medium was supplemented with 10% fetal bovine serum (FBS; Gibco), 100 μM Taurine (Sigma) and 2 mM GlutaMAX (Invitrogen) beginning on D42 unless otherwise noted.

Retinoic Acid Treatment.

To promote photoreceptor maturation, suspension cultures of RCs were supplemented daily with 1 μM all-trans retinoic acid (RA; Sigma) at various time windows: W7-W17; W7-W14 or W10-W14; subsequently, RA concentration was decreased to 0.5 μM.

Immunohistochemistry.

Cells growing on adherent conditions were fixed in 4% paraformaldehyde (PFA; Sigma) for 15 min. RCs were fixed in 4% PFA for 30 min. A human eyeball from a 71-year old person affected by age-related macular degeneration (Old Dominion Eye Foundation) was fixed in 4% PFA for 4 hr. Tissue cryopreservation, sectioning, and immunohistochemistry were performed as previously described[31]. Antibodies against the following proteins were used at the indicated dilutions: LHX2 (goat, 1:200, Santa Cruz, sc-19344), RX (Rabbit, 1:500, Abcam, ab86210), SOX1 (goat, 1:1000, R&D, AF3369), VSX2 (sheep, 1:500, Millipore, AB9016), MCM2 (rabbit, 1:1000, Abcam, ab4461), OTX2 (rabbit, 1:500, Millipore, AB9566), recoverin (rabbit, 1:500, Millipore, AB5585), Caspase 3 (rabbit, 1:500, Cell Signaling, asp175), Hu C/D (mouse, 1:200, Molecular Probes, MP21271), BRN3 (goat, 1:100, Santa Cruz, sc-6026X), TUJ1 (Rabbit, 1:2000, Covance, MRB-435P), MITF (mouse, 1:50, NeoMarkers, MS-771-P1), PROX1 (Rabbit, 1:2000, Millipore, AB5475), CRALBP (mouse, 1:500, Abcam, ab15051), Phospho-Histone H3 (PH3, rabbit, 1:250, Cell Signaling, #9701L), rod-opsin (mouse, 1:100, gift from Dr. David Hicks), L/M opsin (rabbit, 1:50,000, gift from Dr. Jeremy Nathans), S-opsin (rabbit, 1:50,000, gift from Dr. Jeremy Nathans), phosphodiesterase 6 alpha (PDE6α, rabbit, 1:1000, Abcam, ab5659) and beta (PDE6β, rabbit, 1:2000, Thermo Scientific, PA1-722), hRetGCl (rabbit, 1:4000, gift from Dr. Alexander M. Dizhoor), $G_{T1\alpha}$ (rabbit, 1:2000, Santa Cruz, sc-389), rod Cyclic Nucleotide Gated Channel a-subunit (CNGA1, mouse, 1:10, a gift from Dr. Robert S. Molday) and β-subunit (CNGB1, mouse, 1:10, a gift from Dr. Robert S. Molday). Antibodies from the DSHB, developed under the auspices of the NICHD and maintained by The University of Iowa, Department of Biology, were: PAX6 (mouse, 1:50), AP2α (3B5a, mouse, 1:35), and SV2 (mouse, 1:1000). Secondary antibodies used included the corresponding species-specific Alexa Fluor-488, -546 and -647 conjugated antibodies (1:500, Molecular Probes). DAPI was used for nuclear counterstaining (Molecular Probes). Fluorescence images were acquired with an LSM 510 confocal microscope (Zeiss).

Detection of Proliferating Cells.

Click-iT EdU imaging kit (Invitrogen, C10337) was used according to the manufacturer's protocol in order to visualize cells undergoing S-phase during the time-window under study. 3-D RCs were incubated with 50 μg of EdU diluted in PBS for 1 hr or 20 hr, then collected and processed for microscopic imaging. An antibody against the DNA replication licensing factor MCM2 (rabbit, 1:1000, Abcam, ab4461) was used to identify proliferating retinal progenitors, whereas an antibody against Phospho-Histone H3 (PH3, rabbit, 1:250, Cell Signaling, #9701L) was used to identify cells in M phase by immunohistochemistry as described above.

RT-PCR.

Total RNA isolation was done in triplicate with RNAeasy mini kit (Qiagen) and followed by DNase I treatment (Qiagen) to remove potential DNA contamination. RNA quality was evaluated using a NanoDrop1000 spectrophotometer (Thermo Scientific). Reverse transcription was performed using the SuperScript III RT-PCR kit (Invitrogen).

Samples without reverse transcriptase were used as negative controls. PCR was performed with Taq DNA polymerase (Invitrogen) on a PTC-200 Thermal Cycler (Bio-Rad). Cycles (30-40 depending on primer pair) were run at 95° C. denaturation for 20 s, 60° C. annealing for 20 s, and 72° C. extension for 30 s. Subsequent PCR products were run on 2% agarose gels. Primers used were as follows: OCT4 forward 5'-CGAGCAATTTGCCAAGCTCCTGAA-3' (SEQ ID NO:1), reverse 5'-TCGGGCACTGCAG-GAACAAATTC-3' (SEQ ID NO:2); SOX2 forward 5'-CCCCCGGCGGCAATAGCA-3' (SEQ ID NO:3), reverse 5'-TCGGCGCCGGGGAGATACAT-3' (SEQ ID NO:4); PAX6 forward 5'-CGGAGTGAATCA GCTCG-GTG-3' (SEQ ID NO:5), reverse 5'-CCGCT-TATACTGGGCTATTTTGC-3'(SEQ ID NO:6); SIX3 forward 5'-CGAGCAGAAGACGCATTGCTTCAA-3' (SEQ ID NO:7), reverse 5'-CGGCCTTGGCTATCATACAT-CACA-3' (SEQ ID NO:8); LHX2 forward 5'-CAAGATCTCGGACCGCTACT-3' (SEQ ID NO:9), reverse 5'-CCGTGG TCAGCATCTTGTTA-3' (SEQ ID NO:10); RX forward 5'-GAATCTCGAAATCTCAGCCC-3' (SEQ ID NO:11), reverse 5'-CTTCACTAATTTGCTCAG-GAC-3' (SEQ ID NO:12); SIX6 forward 5'-ATTTGGGACGGCGAACAGAAGACA-3' (SEQ ID NO:13), reverse 5'-ATCCTGGATGGGCAACTCAGATGT-3' (SEQ ID NO:14); GAPDH forward 5'-ACCACAGTC-CATGCCATCAC-3' (SEQ ID NO:15), reverse 5'-TCCAC-CACC CTGTTGCTGTA-3' (SEQ ID NO:16).

Flow Cytometry.

Neural retina-domains (NR) collected on D22 from two biological replicates were dissociated into single cells with trypsin, fixed in 1% PFA for 15 minutes, washed with PBS containing 0.04% triton-X-100 and 2% donkey serum, and then incubated for 1 hr at RT in primary antibodies at a concentration of 1 µg of antibody per 1 million cells in PBS with 0.25% triton-X-100 and 2% donkey serum. Cells were then incubated with species-specific Alexa Fluor-488 conjugated secondary antibodies for 30 min, washed, and analyzed using a BD Accuri C6 Flow Cytometer (BD Pharmingen). In all experiments, nonspecific, species-appropriate isotype antibodies were used as controls. Data analysis was performed using BD Accuri C6 software.

Ultrastructural Analysis.

CB-iPSC6.2-derived RCs were fixed in a cold, phosphate-buffered, 2.5% glutaraldehyde/2% paraformaldehyde mixture, post-fixed in 1% osmium tetroxide, dehydrated and embedded in Epon 812. Semi-thin sections were cut for orientation, and ultrathin sections were cut and stained with uranyl acetate and lead citrate and examined using a transmission electron microscope (Hitachi H7600).

Live-Cell Imaging.

CB-iPSC6.2-derived RCs were placed in a 1 mm-gap electroporation cuvette with a plasmid solution (2.3 µg/µl of pCIG plasmid expressing nuclear GFP[32] in PBS) and 4 square pulses of 15 V, 50-ms duration, and 950-ms interval were delivered using an ECM 830 electroporation apparatus (BTX, Holliston, Mass., USA). Immediately after electroporation, RCs were returned to the cell-culture incubator for 36 hr, at the end of which time-lapse microscopy imaging was performed at 2-hr intervals for 48 hr using an LSM 710 confocal laser scanning system (Zeiss) equipped with temperature and $CO_2$ control.

Electrical Recordings from Photoreceptors in RCs.

In room light, a CB-iPSC6.2-derived RC (age W25-W27) was embedded in low-melting agarose gel and sliced into 100-µm-thick slices with a vibratome (Leica VT1000S). Then, in darkness, the eyecup slices were transferred to RC culture medium containing 100-µM 9-cis-retinal (a commercially available analog of 11-cis-retinal) and incubated for 1 hr in a light-proof, 95% $O_2$/5% $CO_2$ cell-culture incubator at 37° C. Afterwards, the RC slices, still under light-proof conditions, were transferred and mounted laterally in the recording chamber. All procedures afterwards were performed in infrared or dim-red light. Perforated-patch recordings were performed at 35-37° C. on a Zeiss upright microscope equipped with infrared DIC optics and imaging. The bath solution (Ames medium equilibrated with 95% $O_2$/5% $CO_2$) was temperature-controlled and ran at ~5 ml/min through the 1-ml experimental chamber. All recordings were in the voltage-clamp mode with $V_{hold}$ at −50 mV, low-pass filtered at 20 Hz (8-pole Bessel) and sampled at 500 Hz. The pipette solution contained (in mM): 110 KCl, 13 NaCl, 2 $MgCl_2$, 1 $CaCl_2$, 10 EGTA, 10 HEPES, 0.125 Amphotericin B, pH 7.2 titrated with KOH. The cells situated at the outer 1-4 layers of cells in the RC slice were chosen for recording because rhodopsin-positive photoreceptors were concentrated in this region. The recorded photoreceptor was stimulated with diffuse white flashes (40-ms duration) from a mercury arc lamp, attenuated with neutral density filters, with intensity calibrated with a radiometer.

Longitudinal Analysis of hiPSCs Differentiation:

Formation of NR Domains.

Aggregates seeded on D7 appeared as colonies under adherent culture conditions. Most colonies had clear boundaries before D20. The percentage of NR domains expressing VSX2 was evaluated by counting the number of VSX2-positive among DAPI-positive colonies on D12, D16 and D20. Colonies containing >5 VSX2-positive cells were considered NR domains. Results represent the average of 3 independent experiments, ~100 colonies per time-point, per cell line, per experiment. To trace the morphological progression of NR and RPE domains, plated aggregates were individually outlined using a microscope objective marker (Nikon) and imaged every other day from D17 to D25 under an inverted microscope (Nikon).

Growth of RCs in Long-Term Culture.

RCs were imaged every 15 days from D45 until D120 under inverted microscope with 4× magnification. The length of the longest axis of RCs was measured using Image J. Results represent the average of 15-20 RCs per time point.

Birthdating of Retinal Cell Types.

To approximate the time of generation of the major retinal neuronal cell types, a minimum of 5 RCs were collected each week from W5 to W13, then every other week until W17, and once a month thereafter. Cell-type-specific markers were used for immunohistochemical identification as described above.

REFERENCES

1. Hartong, D. T., Berson, E. L. & Dryja, T. P. Retinitis pigmentosa. *Lancet* 368, 1795-1809 (2006).
2. Ramsden, C. M. et al. Stem cells in retinal regeneration: past, present and future. Development 140, 2576-2585 (2013).
3 Stern, J. H. & Temple, S. Stem cells for retinal replacement therapy. Neurotherapeutics: the journal of the American Society for Experimental NeuroTherapeutics 8, 736-743 (2011).
4. Cramer, A. O. & MacLaren, R. E. Translating induced pluripotent stem cells from bench to bedside: application to retinal diseases. Current gene therapy 13, 139-151 (2013).

5. Eiraku, M. et al. Self-organizing optic-cup morphogenesis in three-dimensional culture. Nature 472, 51-56 (2011).
6. Nakano, T. et al. Self-formation of optic cups and storable stratified neural retina from human ESCs. Cell Stem Cell 10, 771-785 (2012).
7. Adler, R. & Canto-Soler, M. Molecular mechanisms of optic vesicle development: complexities, ambiguities and controversies. Dev Biol 305, 1-13 (2007).
8. Bassett, E. A. & Wallace, V. A. Cell fate determination in the vertebrate retina. Trends in neurosciences 35, 565-573 (2012).
9. Lamba, D. A., Karl, M. O., Ware, C. B. & Reh, T. A. Efficient generation of retinal progenitor cells from human embryonic stem cells. Proc Natl Acad Sci USA 103, 12769-12774 (2006).
10. Osakada, F. et al. Toward the generation of rod and cone photoreceptors from mouse, monkey and human embryonic stem cells. Nat Biotechnol 26, 215-224 (2008).
11. Osakada, F. et al. In vitro differentiation of retinal cells from human pluripotent stem cells by small-molecule induction. J Cell Sci 122, 3169-3179 (2009).
12. Tucker, B. A. et al. Patient-specific iPSC-derived photoreceptor precursor cells as a means to investigate retinitis pigmentosa. eLife 2, e00824 (2013).
13. Tucker, B. A., Anfinson, K. R., Mullins, R. F., Stone, E. M. & Young, M. J. Use of a synthetic xeno-free culture substrate for induced pluripotent stem cell induction and retinal differentiation. Stem cells translational medicine 2, 16-24 (2013).
14. Boucherie, C. et al. Brief report: self-organizing neuroepithelium from human pluripotent stem cells facilitates derivation of photoreceptors. Stem Cells 31, 408-414 (2013).
15. Zuber, M. E. Eye field specification in *Xenopus laevis*. Curr Top Dev Biol 93, 29-60 (2010).
16. Zhang, X. et al. Pax6 is a human neuroectoderm cell fate determinant. Cell Stem Cell 7, 90-100 (2010).
17. Pevny, L. H., Sockanathan, S., Placzek, M. & Lovell-Badge, R. A role for SOX1 in neural determination. Development 125, 1967-1978 (1998).
18. Xia, X. & Zhang, S. C. Differentiation of neuroepithelia from human embryonic stem cells. Methods Mol Biol 549, 51-58 (2009).
19. Nguyen, M. & Arnheiter, H. Signaling and transcriptional regulation in early mammalian eye development: a link between FGF and MITF. Development 127, 3581-3591 (2000).
20. Horsford, D. J. et al. Chx10 repression of Mitf is required for the maintenance of mammalian neuroretinal identity. Development 132, 177-187 (2005).
21. O'Rahilly, R. M., F. Developmental Stages in Human Embryos. (Carnagie Institution of Washington, 1987).
22. Prada, C., Puga, J., Perez-Mendez, L., Lopez, R. & Ramirez, G. Spatial and Temporal Patterns of Neurogenesis in the Chick Retina. Eur J Neurosci 3, 559-569 (1991).
23. Cepko, C. L., Austin, C. P., Yang, X., Alexiades, M. & Ezzeddine, D. Cell fate determination in the vertebrate retina. Proc Natl Acad Sci USA 93, 589-595 (1996).
24. Stenkamp, D. L., Gregory, J. K. & Adler, R. Retinoid effects in purified cultures of chick embryo retina neurons and photoreceptors. Invest Ophthalmol Vis Sci 34, 2425-2436 (1993).
25. Stevens, C. B., Cameron, D. A. & Stenkamp, D. L. Plasticity of photoreceptor-generating retinal progenitors revealed by prolonged retinoic acid exposure. BMC Dev Biol 11, 51 (2011).
26. Hendrickson, A. et al. Rod photoreceptor differentiation in fetal and infant human retina. Exp Eye Res 87, 415-426 (2008).
27. Hollenberg, M. J. & Spira, A. W. Human retinal development: ultrastructure of the outer retina. The American journal of anatomy 137, 357-385 (1973).
28. Hogan, M. A., J A; Weddell, J. Histology of the Human Eye—An Atlas and textbook. (W. B. Saunders Company, 1971).
29. Meyer, J. S. et al. Optic Vesicle-like Structures Derived from Human Pluripotent Stem Cells Facilitate a Customized Approach to Retinal Disease Treatment. Stem Cells 29, 1206-18 (2011).
30. Phillips, M. J. et al. Blood-derived human iPS cells generate optic vesicle-like structures with the capacity to form retinal laminae and develop synapses. Invest Ophthalmol Vis Sci 53, 2007-2019 (2012).
31. Gutierrez, C., McNally, M. & Canto-Soler, M. V. Cytoskeleton proteins previously considered exclusive to Ganglion Cells are transiently expressed by all retinal neuronal precursors. BMC Dev Biol 11, 46, doi:1471-213X-11-46 [pii]10.1186/1471-213X-11-46 (2011).
32. Megason, S. G. & McMahon, A. P. A mitogen gradient of dorsal midline Wnts organizes growth in the CNS. Development 129, 2087-2098 (2002).
33. Burridge, P. W. et al. A universal system for highly efficient cardiac differentiation of human induced pluripotent stem cells that eliminates interline variability. PLoS ONE 6, e18293, doi:10.1371/journal.pone.0018293 (2011).
34. Park, T. S. et al. Growth factor-activated stem cell circuits and stromal signals cooperatively accelerate non-integrated iPSC reprogramming of human myeloid progenitors. PLoS One 7, e42838, doi:10.1371/journal.pone.0042838 (2012).
35. Yan, X. X. & Wiechmann, A. F. Early expression of recoverin in a unique population of neurons in the human retina. Anatomy and embryology 195, 51-63 (1997).
36. Glubrecht, D. D., Kim, J. H., Russell, L., Bamforth, J. S. & Godbout, R. Differential CRX and OTX2 expression in human retina and retinoblastoma. J Neurochem 111, 250-263, doi:10.1111/j.1471-4159.2009.06322.x (2009).

We claim:

1. An in vitro method for differentiating human induced pluripotent stem cells (hiPSCs) into three-dimensional retinal tissue comprising functional photoreceptors, the method comprising the steps of:
   a. on day 0 of differentiation:
      i. enzymatically detaching hiPSCs cultured on extracellular matrix-coated cell culture substrates with feeder-free cell culture medium, and
      ii. culturing the hiPSCs in suspension to induce formation of aggregates;
   b. during days 1-3 of differentiation, transitioning the aggregates into neural induction medium (NIM);
   c. during day 6 or 7, seeding the aggregates on to extracellular matrix-coated cell culture substrates;
   d. at any time between day 14 and day 17, replacing NIM with a chemically-defined differentiation medium;
   e. during the fourth week of differentiation:
      i. detaching neural retina (NR) domains, and
      ii. culturing in suspension;
   f. during the fifth or sixth week of differentiation, adding animal serum or plasma component to promote cell survival; and
   g. at any time between week 5 and week 14, adding all-trans retinoic acid to induce photoreceptor maturation.

2. The method of claim 1, wherein the all-trans retinoic acid of step (g) is added at a concentration of about 1 μM.

3. The method of claim 2, wherein the all-trans retinoic acid of step (g) is added for a period of about 30 days.

4. The method of claim 3, further comprising the step of (h) decreasing the concentration of all-trans retinoic acid to about 0.5 μM.

5. The method of claim 4, wherein the all-trans retinoic acid is added at any time between week 9 and week 10 at a concentration of about 1 μM and then decreased to about 0.5 μM at any time between week 13 and week 14.

6. The method of claim 4, wherein the all-trans retinoic acid is added on day 63 at a concentration of about 1 μM and then decreased to about 0.5 μM at any time between day 90 and day 98.

7. The method of claim 1, wherein the all-trans retinoic acid is added at any time between week 5 and week 6 at a concentration of about 1 μM and then decreased to about 0.5 at any time between week 13 and week 14.

8. The method of claim 1, wherein the all-trans retinoic acid is added on day 42 at a concentration of about 1 μM and then decreased to about 0.5 μM at any time between day 90 and day 98.

9. The method of claim 1, wherein the enzymatic detachment of step (a)(i) is accomplished using dispase.

10. The method of claim 1, wherein the extracellular matrix is Matrigel™.

11. The method of claim 1, wherein the cell culture substrate is a flask, plate or petri dish.

12. The method of claim 1, wherein the feeder-free cell culture medium is mTeSR™1 medium.

13. The method of claim 1, wherein the NIM of step (b) comprises Dulbecco's modified eagle medium (DMEM)/F12 (1:1), 1% N2 supplement, 1× minimum essential media-non essential amino acids (NEAA), and 2 μg ml$^{-1}$ heparin.

14. The method of claim 1, wherein the chemically-defined differentiation medium of step (d) comprises DMEM/F12 (3:1), 2% B27 (without vitamin A), 1× minimum essential media-non essential amino acids (NEAA), and 1% antibiotic-antimycotic.

15. The method of claim 1, wherein the detachment of step (e) comprises manual detachment.

16. The method of claim 1, wherein the animal serum or plasma component is fetal bovine serum.

17. The method of claim 1, wherein the hiPSCs are selected from the group consisting of CB-iPSC6.2, KA.1 and IMR90-4.

18. The three-dimensional retinal tissue produced by the method of claim 1.

19. An in vitro method for differentiating human induced pluripotent stem cells (hiPSCs) into three-dimensional retinal tissue comprising functional photoreceptors, the method comprising the steps of:
   a. culturing the hiPSCs to form aggregates;
   b. transitioning the aggregates into a neural induction medium;

c. seeding the aggregates on to extracellular matrix coated cell culture substrates;
d. replacing NIM with a chemically-defined differentiation medium;
e. detaching NR domains;
f. culturing in suspension; and
g. adding animal serum or plasma component and all-trans retinoic acid.

20. The method of claim 19, wherein the hiPSCs were cultured on extracellular matrix coated cell culture substrates with feeder-free cell culture medium and enzymatically detached prior to step (a).

21. The method of claim 20, wherein the extracellular matrix is Matrigel™.

22. The method of claim 20, wherein the feeder-free cell culture medium is mTeSR™1 medium.

23. The method of claim 20, wherein the cell culture substrate is a flask, plate or petri dish.

24. The method of claim 20, wherein the enzymatic detachment step is accomplished using dispase.

25. The method of claim 19, wherein step (b) is performed during days 1-3 of differentiation.

26. The method of claim 19, wherein the NIM of step (b) comprises Dulbecco's modified eagle medium (DMEM)/F12 (1:1), 1% N2 supplement, 1× minimum essential media-non essential amino acids (NEAA), and 2 µg ml$^{-1}$ heparin.

27. The method of claim 19, wherein step (c) is performed during day 6 or 7.

28. The method of claim 19, wherein step (d) is performed at any time between day 14 and day 17.

29. The method of claim 19, wherein the chemically-defined differentiation medium of step (d) comprises DMEM/F12 (3:1), 2% B27 (without vitamin A), lx minimum essential media-non essential amino acids (NEAA), and 1% antibiotic-antimycotic.

30. The method of claim 19, wherein the detachment of step (e) comprises manual detachment.

31. The method of claim 19, wherein the animal serum or plasma component is fetal bovine serum.

32. The method of claim 19, wherein the all-trans retinoic acid of step (g) is added at a concentration of about 1 µM.

33. The method of claim 32, wherein the all-trans retinoic acid of step (g) is added for a period of about 30 days.

34. The method of claim 33, further comprising the step of (h) decreasing the concentration of all-trans retinoic acid to about 0.5 µM.

35. The method of claim 34, wherein the all-trans retinoic acid is added at any time between week 9 and week 10 at a concentration of about 1 µM and then decreased to about 0.5 µM at any time between week 13 and week 14.

36. The method of claim 34, wherein the all-trans retinoic acid is added on day 63 at a concentration of about 1 µM and then decreased to about 0.5 µM at any time between day 90 and day 98.

37. The method of claim 19, wherein the all-trans retinoic acid is added at any time between week 5 and week 6 at a concentration of about 1 µM and then decreased to about 0.5 µM at any time between week 13 and week 14.

38. The method of claim 19, wherein the all-trans retinoic acid is added on day 42 at a concentration of about 1 µM and then decreased to about 0.5 µM at any time between day 90 and day 98.

39. The method of claim 19, wherein the hiPSCs are selected from the group consisting of CB-iPSC6.2, KA.1 and IMR90-4.

40. The three-dimensional retinal tissue produced by the method of claim 19.

41. An in vitro method for differentiating human induced pluripotent stem cells (hiPSCs) into three-dimensional retinal tissue comprising functional photoreceptors, the method comprising the steps of:
a. on day 0 of differentiation:
i. enzymatically detaching hiPSCs cultured on Matrigel-coated plates with mTeSR™1 medium, and
ii. culturing the hiPSCs in suspension to induce formation of aggregates;
b. during days 1-3 of differentiation, transitioning the aggregates into neural induction medium (NIM);
c. seeding the aggregates on to Matrigel-coated dishes on day 7;
d. on day 16, replacing NIM with a chemically-defined differentiation medium; and
e. on the fourth week of differentiation:
i. detaching neural retina (NR) domains, and
ii. culturing in suspension;
f. at any time between day 30 and 42, adding fetal bovine serum to promote cell survival;
g. adding 1 µM all-trans retinoic acid on day 63, to induce photoreceptor maturation; and
h. decreasing the concentration of all-trans retinoic acid to 0.5 µM at any time between day 90 and day 98.

42. The three-dimensional retinal tissue produced by the method of claim 41.

* * * * *

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
```

<223> OTHER INFORMATION: OCT4 forward primer

<400> SEQUENCE: 1
cgagcaattt gccaagctcc tgaa                                          24

<210> SEQ ID NO 2
<211> LENGTH: 23
<212> TYPE: DNA
<213> ORGANISM: Artificial Sequence
<220> FEATURE:
<223> OTHER INFORMATION: OCT4 reverse primer

<400> SEQUENCE: 2
tcgggcactg caggaacaaa ttc                                           23

<210> SEQ ID NO 3
<211> LENGTH: 18
<212> TYPE: DNA
<213> ORGANISM: Artificial Sequence
<220> FEATURE:
<223> OTHER INFORMATION: SOX2 forward primer

<400> SEQUENCE: 3
cccccggcgg caatagca                                                 18

<210> SEQ ID NO 4
<211> LENGTH: 20
<212> TYPE: DNA
<213> ORGANISM: Artificial Sequence
<220> FEATURE:
<223> OTHER INFORMATION: SOX2 reverse primer

<400> SEQUENCE: 4
tcggcgccgg ggagatacat                                               20

<210> SEQ ID NO 5
<211> LENGTH: 20
<212> TYPE: DNA
<213> ORGANISM: Artificial Sequence
<220> FEATURE:
<223> OTHER INFORMATION: PAX6 forward primer

<400> SEQUENCE: 5
cggagtgaat cagctcggtg                                               20

<210> SEQ ID NO 6
<211> LENGTH: 23
<212> TYPE: DNA
<213> ORGANISM: Artificial Sequence
<220> FEATURE:
<223> OTHER INFORMATION: PAX6 reverse primer

<400> SEQUENCE: 6
ccgcttatac tgggctattt tgc                                           23

<210> SEQ ID NO 7
<211> LENGTH: 24
<212> TYPE: DNA
<213> ORGANISM: Artificial Sequence
<220> FEATURE:
<223> OTHER INFORMATION: SIX3 forward primer

<400> SEQUENCE: 7
cgagcagaag acgcattgct tcaa                                          24

```
<210> SEQ ID NO 8
<211> LENGTH: 24
<212> TYPE: DNA
<213> ORGANISM: Artificial Sequence
<220> FEATURE:
<223> OTHER INFORMATION: SIX3 reverse primer

<400> SEQUENCE: 8
cggccttggc tatcatacat caca                                              24

<210> SEQ ID NO 9
<211> LENGTH: 20
<212> TYPE: DNA
<213> ORGANISM: Artificial Sequence
<220> FEATURE:
<223> OTHER INFORMATION: LHX2 forward primer

<400> SEQUENCE: 9
caagatctcg gaccgctact                                                   20

<210> SEQ ID NO 10
<211> LENGTH: 20
<212> TYPE: DNA
<213> ORGANISM: Artificial Sequence
<220> FEATURE:
<223> OTHER INFORMATION: LHX2 reverse primer

<400> SEQUENCE: 10
ccgtggtcag catcttgtta                                                   20

<210> SEQ ID NO 11
<211> LENGTH: 20
<212> TYPE: DNA
<213> ORGANISM: Artificial Sequence
<220> FEATURE:
<223> OTHER INFORMATION: RX forward primer

<400> SEQUENCE: 11
gaatctcgaa atctcagccc                                                   20

<210> SEQ ID NO 12
<211> LENGTH: 21
<212> TYPE: DNA
<213> ORGANISM: Artificial Sequence
<220> FEATURE:
<223> OTHER INFORMATION: RX reverse primer

<400> SEQUENCE: 12
cttcactaat ttgctcagga c                                                 21

<210> SEQ ID NO 13
<211> LENGTH: 24
<212> TYPE: DNA
<213> ORGANISM: Artificial Sequence
<220> FEATURE:
<223> OTHER INFORMATION: SIX6 forward primer

<400> SEQUENCE: 13
atttgggacg gcgaacagaa gaca                                              24

<210> SEQ ID NO 14
<211> LENGTH: 24
<212> TYPE: DNA
<213> ORGANISM: Artificial Sequence
<220> FEATURE:
<223> OTHER INFORMATION: SIX6 reverse primer
```

```
<400> SEQUENCE: 14
atcctggatg ggcaactcag atgt                                            24

<210> SEQ ID NO 15
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 15
accacagtcc atgccatcac                                                 20

<210> SEQ ID NO 16
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 16
tccaccaccc tgttgctgta                                                 20
```